US010786227B2

(12) United States Patent
Sakanashi et al.

(10) Patent No.: US 10,786,227 B2
(45) Date of Patent: Sep. 29, 2020

(54) SYSTEM AND METHOD FOR ULTRASOUND EXAMINATION

(71) Applicant: National Institute of Advanced Industrial Science and Technology, Tokyo (JP)

(72) Inventors: Hidenori Sakanashi, Tsukuba (JP); Hirokazu Nosato, Tsukuba (JP); Masaya Iwata, Tsukuba (JP); Eiichi Takahashi, Tsukuba (JP); Yuudai Yamazaki, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 600 days.

(21) Appl. No.: 15/532,008

(22) PCT Filed: Dec. 1, 2015

(86) PCT No.: PCT/JP2015/083773
§ 371 (c)(1),
(2) Date: May 31, 2017

(87) PCT Pub. No.: WO2016/088758
PCT Pub. Date: Jun. 9, 2016

(65) Prior Publication Data
US 2017/0258451 A1     Sep. 14, 2017

(30) Foreign Application Priority Data
Dec. 1, 2014   (JP) ................................. 2014-243189

(51) Int. Cl.
*A61B 8/08*   (2006.01)
*G06T 7/00*   (2017.01)

(52) U.S. Cl.
CPC ............... *A61B 8/5223* (2013.01); *A61B 8/08* (2013.01); *A61B 8/085* (2013.01); *A61B 8/5246* (2013.01);
(Continued)

(58) Field of Classification Search
None
See application file for complete search history.

(56) References Cited
U.S. PATENT DOCUMENTS 6,309,353 B1   10/2001   Cheng et al.
9,003,880 B2 *   4/2015   Sbihli ................. G01N 27/902
73/488
(Continued)

FOREIGN PATENT DOCUMENTS

EP   2 402 745   1/2012
JP   07-299068   11/1995
(Continued)

OTHER PUBLICATIONS

Zhang et al, "Tumoe segmentation from magnetic resonance imaging by learning via one-class support vector machine", International Workshop on Advanced Image Technology (IWAIT '04), Jan. 2004, Singapore, Singapore. pp. 207-211 (Year: 2004).*
(Continued)

*Primary Examiner* — Katherine L Fernandez
*Assistant Examiner* — Yi-Shan Yang
(74) *Attorney, Agent, or Firm* — Rankin, Hill & Clark LLP

(57) ABSTRACT

The ultrasound examination system automatically detects a lesion, based on a dynamic image including a plurality of frame arrays that are temporally continuous and are output from the ultrasound examination apparatus with an ultrasonic probe being manipulated. Detection accuracy of the ultrasound examination system can be increased. A feature
(Continued)

extractor in a frame checker extracts cubic higher-order local autocorrelation features from each frame of a plurality frames that constitute a dynamic image of a human body part as obtained from an ultrasound examination apparatus while an examiner manipulates an ultrasonic probe on the examinee. A final determinator determines that the frame in question is a normal frame when a speed determinator determines that the speed of the ultrasonic probe is not a normal speed even though the frame in question can be determined as an abnormal frame containing a lesion.

12 Claims, 16 Drawing Sheets

(52) U.S. Cl.
CPC .. *G06T 7/0012* (2013.01); *G06T 2207/10132* (2013.01)

(56) References Cited

U.S. PATENT DOCUMENTS

| | | | | |
|---|---|---|---|---|
| 2006/0058919 | A1* | 3/2006 | Sommer | A61B 6/0457 700/245 |
| 2008/0123975 | A1* | 5/2008 | Otsu | G06K 9/00342 382/236 |
| 2010/0185092 | A1 | 7/2010 | Yao et al. | |
| 2011/0182495 | A1* | 7/2011 | Sun | G06T 7/0004 382/141 |
| 2013/0094733 | A1 | 4/2013 | Nosato et al. | |
| 2014/0140593 | A1 | 5/2014 | Park et al. | |
| 2014/0163369 | A1* | 6/2014 | Nair | A61B 5/4869 600/437 |
| 2016/0019441 | A1* | 1/2016 | Ryu | A61B 8/5207 382/131 |

FOREIGN PATENT DOCUMENTS

| | | |
|---|---|---|
| JP | 2000-126182 | 5/2000 |
| JP | 2010-166973 | 8/2010 |
| JP | 2011-014152 | 1/2011 |
| JP | 2014-100569 | 6/2014 |
| WO | 2012/011579 | 1/2012 |
| WO | 2014/099825 | 6/2014 |
| WO | 2014/179277 | 11/2014 |

OTHER PUBLICATIONS

Vlasveld, "Introduction to One-class Support Vector Machines", http://rvlasveld.github.io/blog/2013/07/12/introduction-to-one-class-support-vector-machines/, Jul. 12, 2013. (Year: 2013).*

Yudai Yamazaki et al., "A Study on Lesion Detection from Breast Ultrasound Images Based on Difference of Texture Change between Adjacent Regions", IEICE Technical Report, vol. 114, No. 482, Feb. 23, 2015, Listed in International Search Report, 2 pages.

Yudai Yamazaki et al., "Koji Kyokusho Jiko Sokan Tokucho ni Motozuku AdaBoost o Michiita Nyusen Choonpa Gazo karano shuryuzo Kenshutsu", Information Processing Society of Japan Dai 75 Kai Zenkoku Taikai Koen Ronbunshu (4), Mar. 6, 2013, (Mar. 6, 2013), Listed in International Search Report, English abstract included, 3 pages.

International Search Report dated Feb. 16, 2016 (Feb. 16, 2016), 2 pages.

* cited by examiner

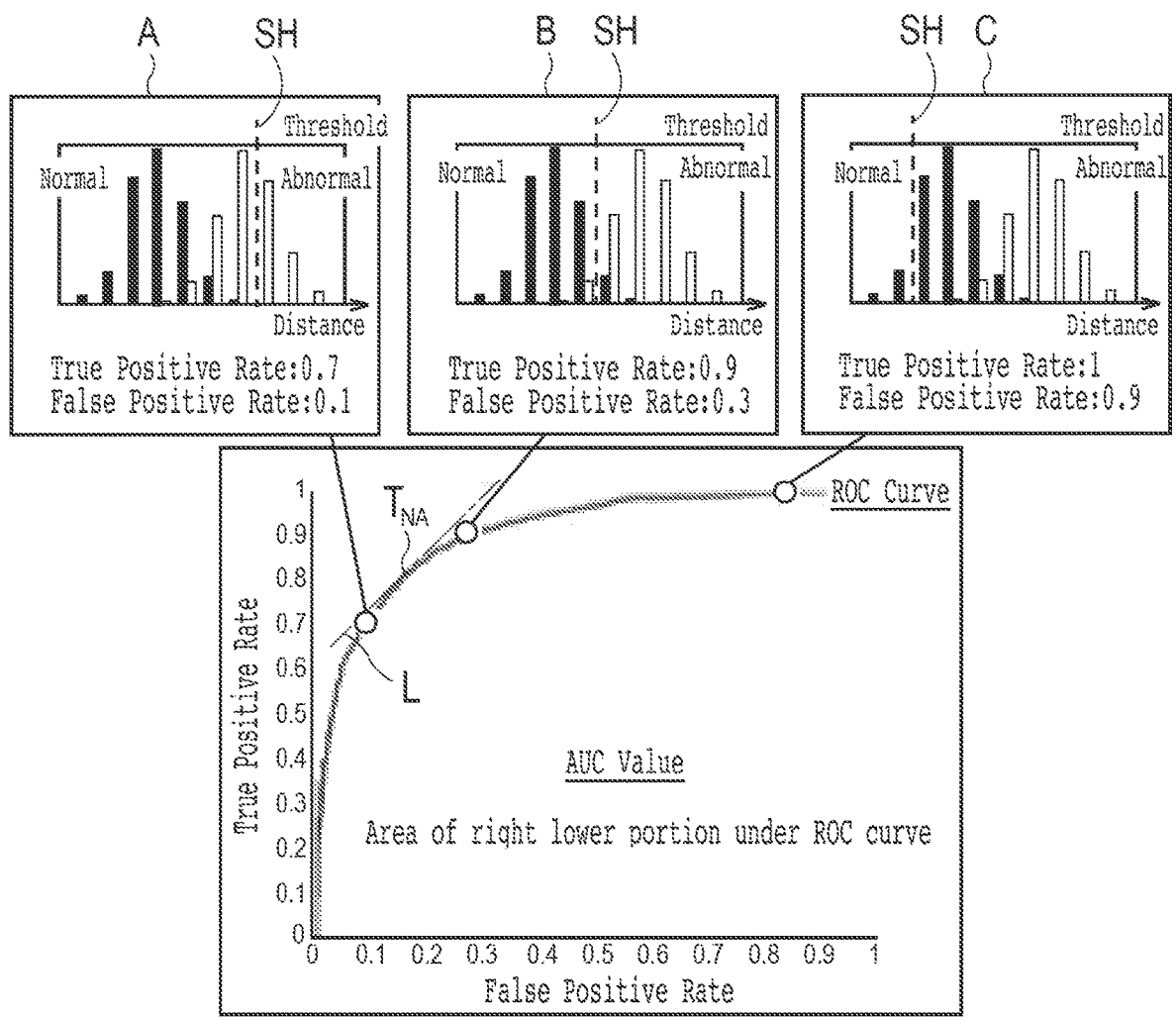

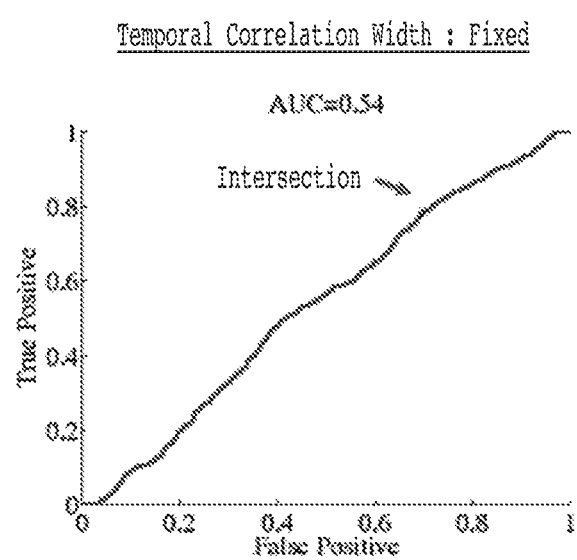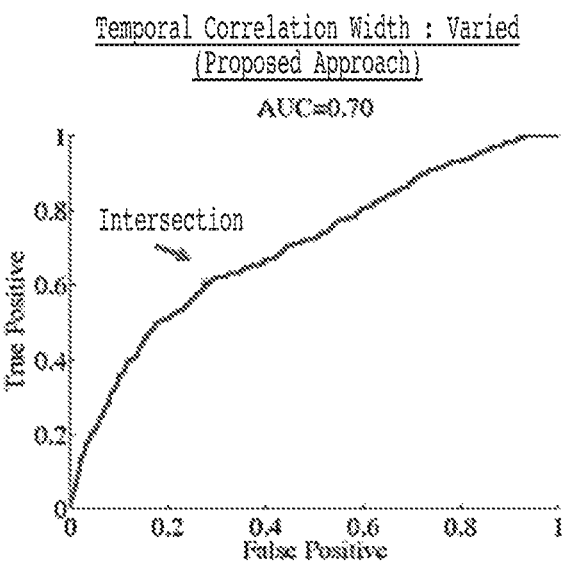
Fig.12A
Fig.12B

SYSTEM AND METHOD FOR ULTRASOUND EXAMINATION

TECHNICAL FIELD

The present invention relates to a system and a method for ultrasound examination intended to examine whether a frame in question of a dynamic image is a normal frame not containing a lesion or an abnormal frame containing a lesion, based on the dynamic image comprised of a plurality of frame arrays that are temporally continuous and are output from an ultrasound examination apparatus.

BACKGROUND ART

In an ultrasound examination apparatus, measurement results are displayed as a dynamic image. In an ultrasound examination for mammary glands, for example, a tumor is depicted as a dark shadowed block and it can accordingly be detected even when each frame of the dynamic image is separately handled as a static image. In a method for detecting abnormality from static images (pathological images) as disclosed in Patent Document 1 (WO2012011579), a tumor can be discovered. In such method, however, the shapes of non-mass image-forming lesions are not clear and it is necessary to observe texture changes represented by the mammary tissues. For this reason, the approach disclosed in Patent Document 1 cannot deal with non-mass image-forming lesions. A further method is required, that is, pattern recognition of dynamic images such as correlation measurement of preceding and following frames of the frame in question.

Patent Document 2 (JP2000-126182A) discloses a method for determining whether or not an image in question is a tumor, based on the ratio of a surface area and a volume of the image in question by mounting a position sensor on an ultrasonic probe and constructing three-dimensional data of the internal structure of a human body by combining image information with position information. Patent Document 3 (JP2010-166973A) discloses a method for estimating a position by analyzing an acquired image instead of mounting a position sensor on an ultrasonic probe.

RELATED ART DOCUMENTS

Patent Documents

Patent Document 1: WO2012011579
Patent Document 2: JP2000-126182A
Patent Document 3: JP2010-166973A

SUMMARY OF INVENTION

Technical Problems

The method disclosed in Patent Document 2 is directed only to clearly shaped tumors, not to non-mass image-forming lesions having unclear shapes.

The method disclosed in Patent Document 3 indicates estimated position information as a body mark on a screen for helping an examiner to readily grasp an examined body part, but does not utilize it for automatic detection of a lesion.

Accordingly, an object of the present invention is to increase detection accuracy of an ultrasound examination system in automatically detecting a lesion, based on a dynamic image comprised of a plurality of frame arrays that are temporally continuous and are output from an ultrasound examination apparatus as an ultrasonic probe is manipulated.

Another object of the present invention is to increase detection accuracy of an ultrasound examination method for automatically detecting a lesion, based on a dynamic image comprised of a plurality of frame arrays that are temporally continuous and are output from an ultrasound examination apparatus with an ultrasonic probe being manipulated.

Solution to Problems

In a first aspect of the present invention, an ultrasound examination system (hereinafter referred to as an ultrasound examination system of the first invention) is provided. The ultrasound examination system of the first invention is intended to examine whether or not a lesion exists, based on a dynamic image comprised of a plurality of frame arrays that are temporally continuous and are output from an ultrasound examination apparatus with an ultrasonic probe being manipulated. The system comprises a reference data storage, a frame checker, a speed information acquirer, and a speed determinator (determiner). The reference data storage is operable to store reference data for determining normality that are obtained by learning in advance, specifically by extracting cubic higher-order local autocorrelation features from a plurality of frames that constitute a dynamic image of a human body part where a lesion does not exist as obtained from a reference examinee or an examinee with an ultrasonic probe being manipulated at a speed within a predetermined speed range and analyzing extraction results using a predetermined analyzing method. An arbitrary method may be employed as the predetermined analyzing method. For example, a subspace method and one-class SVM (Support Vector Machine) may be used. The speed information acquirer is operable to acquire speed information on a speed of the ultrasonic probe manipulated by the examiner in respect of each frame. The speed determinator is operable to determine that the speed of the ultrasonic probe, which has been obtained from the speed information acquired by the speed information acquirer, is a normal speed when the speed of the ultrasonic probe does not exceed a threshold predefined with reference to a speed within the predetermined speed range when a dynamic image has been acquired by learning in advance. Here, the predefined threshold used in the speed determinator is defined based on speeds within the predetermined speed range at the time of acquiring the dynamic image used in learning in advance.

The frame checker includes a feature extractor and a state determinator (determiner). The feature extractor is operable to extract cubic higher-order local autocorrelation features from each of a plurality of frames that constitute a dynamic image of a human body part as obtained from the ultrasound examination apparatus when an examiner manipulates the ultrasonic probe on the examinee. The state determinator is operable to determine whether a frame in question is a normal frame not containing the lesion or an abnormal frame containing the lesion, based on extraction results of cubic higher-order local autocorrelation features from each frame and the reference data for determining normality. More specifically, the state determinator determines that the frame in question is a normal frame when the speed determinator determines that the speed of the ultrasonic probe is not the normal speed even though the frame in question can be determined as an abnormal frame, based only on the extraction results of cubic higher-order local autocorrelation features from each frame and the reference data for determining normality. The inventors have found that when the speed of the ultrasonic probe increases, a feature, which is very similar to a feature indicative of a frame where a lesion exists, is likely to appear regardless of whether or not a lesion actually exists. Based on the findings, it should be determined that the frame in question is the normal frame when the speed determinator determines that the speed of the ultrasonic probe is not the normal speed even though the frame in question can be determined as an abnormal frame, based only on the extraction results of cubic higher-order local autocorrelation features from each frame and the reference data for determining normality. As a result, according to the first invention, erroneous detections can significantly be reduced. The frame checker may be implemented by using a computer.

In a second aspect of the present invention, an ultrasound examination system (hereinafter referred to as an ultrasound examination system of the second invention) is provided. The ultrasound examination apparatus of the second invention comprises a reference data storage, a frame checker, and a speed information acquirer. The reference data storage is operable to store reference data for determining normality that are obtained by extracting cubic higher-order local autocorrelation features from a plurality of frames that constitute a dynamic image of a human body part where a lesion does not exist as obtained from a reference examinee or an examinee with an ultrasonic probe being manipulated at a speed within a predetermined speed range, and analyzing the extraction results using a predetermined method. The speed information acquirer is operable to acquire speed information on a speed of the ultrasonic probe manipulated by the examiner in respect of each frame. The frame checker includes a feature extractor and a state determinator (determiner). The feature extractor is operable to extract cubic higher-order local autocorrelation features from each of a plurality of frames that constitute a dynamic image of a human body part as obtained from the ultrasound examination apparatus while an examiner manipulates the ultrasonic probe on the examinee. The state determinator is operable to determine whether a frame in question is a normal frame not containing the lesion or an abnormal frame containing the lesion, based on extraction results of cubic higher-order local autocorrelation features from each frame and the reference data for determining normality. Especially, the feature extractor in the frame checker has a function of adjusting a temporal correlation width indicative of a correlation width in a temporal direction so as to suppress an influence of changes in the speed of the ultrasonic probe to be given to the extraction results, based on the speed information on the speed of the ultrasonic probe. Then, the state determinator in the frame checker determines whether the frame in question is the normal frame or the abnormal frame, based only on the extraction results of cubic higher-order local autocorrelation features from each frame and the reference data for determining normality. According to the second invention, as with the first invention, erroneous detections of abnormal frames can significantly be reduced by adjusting the temporal correlation width so as to suppress the influence of changes in speed of the ultrasonic probe to be given to extraction results. Generally, the cubic higher-order local autocorrelation features extracted from the frames of a dynamic image include not only information on cubic structures obtainable by continuously representing sectional images of the inside of an examinee's human body but also information on the scanning speed of an ultrasonic probe manipulated by an examiner. The latter information hardly contributes to detection of a lesion. In other words, the latter information that is merely noise can be suppressed in the second invention, thereby significantly reducing erroneous detections.

In the first invention, if the predetermined analyzing method is a subspace method, the reference data storage stores, as the reference data for determining normality, a normal subspace obtained by performing principal component analysis on the extraction results of each frame. The state determinator in the frame checker includes a distance calculator, a distance determinator (determiner), and a final determinator (determiner). The distance calculator is operable to calculate a distance between the extraction results of cubic higher-order local autocorrelation features from each frame and the reference data for determining normality (the normal subspace). The distance determinator is operable to determine whether or not the distance is a normal distance, based on whether or not the distance exceeds a predefined threshold. The final determinator is operable to determine that the frame in question is the normal frame when the distance determinator determines that the distance is the normal distance and when the distance determinator determines that the distance is not the normal distance and the speed determinator determines that the speed is not the normal speed (the speed exceeds the predefined threshold), and is operable to determine that the frame in question is the abnormal frame when the distance determinator determines that the distance is not the normal distance and the speed determinator determines that the speed is the normal speed. If the subspace method is employed as the analyzing method, it can quickly be determined whether or not the distance is normal.

In the second invention, the reference data storage is operable to store reference data for determining normality that are obtained by extracting cubic higher-order local autocorrelation features from a plurality of frames that constitute a dynamic image of a human body part where a lesion does not exist as obtained from a reference examinee or an examinee with an ultrasonic probe being manipulated while adjusting a temporal correlation width indicative of a correlation width in a temporal direction so as to suppress an influence of changes in a speed of the ultrasonic probe to be given to extraction results, based on speed information on the speed of the ultrasonic probe, and analyzing extraction results using a predetermined analyzing method. The feature extractor in the frame checker adjusts the temporal correlation width in a weakly monotonically decreasing manner according to a magnitude of the speed of the ultrasonic probe that is obtained from the speed information. Specifically, it is preferred that the feature extractor prepares a plurality of speed threshold ranges that stepwisely increase in value and a plurality of temporal correlation widths corresponding to the plurality of speed threshold ranges, compares the speed of the ultrasonic probe with the plurality of speed threshold ranges, and selects the temporal correlation width corresponding the speed of the ultrasonic probe.

As a predetermined method to be used in calculating the reference data for determining normality, a one-class SVM (Support Vector Machine) may be employed. When this method is employed, only normal frames are leaned to define support vectors representative of normal classes as the reference data for determining normality; and the frame checker determines whether or not the frame in question is the normal frame according to whether or not analyzed data of the frame in question fall in the normal classes. The use of this method increases detection accuracy, compared with the subspace method.

The speed information acquirer may arbitrarily acquire speed information on the speed of the ultrasonic probe by means of a speed sensor, for example. When utilizing an ultrasound examination apparatus equipped with a function of detecting the position and angle of an ultrasonic probe on a real time basis for the purpose of supporting an examiner by displaying information and images in conjunction with the X-ray CT and MRI images, the speed information may be calculated from the position and posture information on the ultrasonic probe.

The predefined threshold used in the distance determinator is defined by ROC (Receiver Operating Characteristic) analysis. Generally, in evaluating the performance of an abnormality detector (an apparatus for detecting abnormality), it is preferred that the true positive rate (a probability that examination shows true positivity for patients is high and the false positive rate (a probability that examination shows positivity for healthy people) is low. A high true positive rate and a low false positive rate have a trade-off relationship, and they hardly go together. If the threshold is lowered to increase the true positive rate, erroneous (over) detections (positivity is shown for healthy people) will increase, thereby increasing the false positive rate. Conversely, if the threshold is raised to suppress the false positive rate at a low level, erroneous (overlooked) detections (negativity is shown for patients) tend to increase, thereby lowering the true positive rate. The ROC analysis is widely used in analyzing the relationship between the two rates when the threshold is varied. The use of ROC analysis can facilitate determination of an appropriate balance between the two rates.

The predefined threshold $T_s$ used in the speed determinator is represented by an expression of $T_s=u+k\times\sigma$ where u stands for an average moving speed of the ultrasonic probe in learned dynamic images, $\sigma$ for the standard deviation of the average moving speed, and k for a parameter determined by an experiment. If the threshold $T_s$ is defined in this manner, a general speed range when an examiner manipulates an ultrasonic probe (a predetermined speed range) can be calculated from the speed of the ultrasonic probe in learned dynamic images and it can be determined whether or not a particular speed deviates from the general speed.

The first invention can be identified as a computer-implemented method for ultrasound examination intended to examine whether or not a lesion exists, based on a dynamic image comprised of a plurality of frame arrays that are temporally continuous and are output from an ultrasound examination apparatus with an ultrasonic probe being manipulated. The method uses a computer to execute the steps of learning, extracting features, checking a frame in question, acquiring speed information, and determining a speed. In the step of learning, reference data for determining normality are obtained by learning and are stored in a reference data storage by extracting cubic higher-order local autocorrelation features from a plurality of frames that constitute a dynamic image of a human body part where a lesion does not exist as obtained from a reference examinee or an examinee with an ultrasonic probe being manipulated, and analyzing extraction results by a predetermined method. In the step of extracting features, cubic higher-order local autocorrelation features are extracted from each of a plurality of frames that constitute a dynamic image of a human body part that have been obtained from the ultrasound examination apparatus while an examiner manipulates the ultrasonic probe on the examinee. In the step of checking a frame in question, it is determined whether the frame in question is a normal frame not containing the lesion or an abnormal frame containing the lesion, based on extraction results of cubic higher-order local autocorrelation features from each frame and the reference data for determining normality. In the step of acquiring speed information, speed information on a speed of the ultrasonic probe manipulated by the examiner in respect of each frame is acquired. In the step of determining a speed, it is determined that the speed of the ultrasonic probe, which has been obtained from the speed information acquired in the step of acquiring speed information, is a normal speed when the speed of the ultrasonic probe does not exceed a threshold defined with reference to the predetermined speed range. Especially in the step of checking a frame in question, it is determined that the frame in question is the normal frame when it is determined in the step of determining a speed that the speed of the ultrasonic probe is not the normal speed even though the frame in question can be determined as an abnormal frame, based only on the extraction results of cubic higher-order local autocorrelation features from each frame and the reference data for determining normality.

If the predetermined method is a subspace method, and a normal subspace obtained by performing principal component analysis on the extraction results of each frame is stored as the reference data for determining normality in the reference data storage, the step of checking a frame in question includes the steps of calculating a distance, determining a distance, and determining a state. In the step of calculating a distance, a distance between the normal subspace and a subspace obtained by analyzing extraction results of cubic higher-order local autocorrelation features from each frame is calculated. In the step of determining a distance, it is determined whether or not the distance is the normal distance, based on whether or not the distance exceeds a predefined threshold. In the step of determining a state, it is determined that the frame in question is the normal frame when it is determined in the step of determining a distance that the distance is the normal distance and when it is determined in the step of determining a distance that the distance is not the normal distance and it is determined in the step of determining a speed that the speed is not the normal speed, and that the frame in question is the abnormal frame when it is determined in the step of determining a distance that the distance is not the normal distance and it is determined in the step of determining a speed that the speed is the normal speed.

The second invention can be identified as a computer-implemented method for ultrasound examination intended to examine whether or not a lesion exists, based on a dynamic image comprised of a plurality of frame arrays that are temporally continuous and are output from an ultrasound examination apparatus with an ultrasonic probe being manipulated. The method for ultrasound examination of the second invention comprises the steps of learning, extracting features, checking a frame in question, and acquiring speed information.

In the step of learning, reference data for determining normality are obtained by learning and are stored in a reference data storage. The reference data for determining normality are obtained by extracting cubic higher-order local autocorrelation features from a plurality of frames that constitute a dynamic image of a human body part where a lesion does not exist as obtained from a reference examinee or an examinee with an ultrasonic probe being manipulated, while adjusting a temporal correlation width indicative of a correlation width in a temporal direction so as to suppress an influence of changes in the speed of the ultrasonic probe to be given to the extraction results, based on speed information on the speed of the ultrasonic probe, and analyzing extraction results by a predetermined method. In the step of extracting features, cubic higher-order local autocorrelation features are extracted from each of a plurality of frames that constitute a dynamic image of a human body part as obtained from the ultrasound examination apparatus while an examiner manipulates the ultrasonic probe on the examinee. In the step of checking a frame in question, it is determined by using a computer whether a frame in question is a normal frame not containing the lesion or an abnormal frame containing the lesion, based on extraction results of cubic higher-order local autocorrelation features from each frame and the reference data for determining normality. In the step of acquiring speed information, speed information is acquired regarding a speed of the ultrasonic probe manipulated by the examiner in respect of each frame. Especially, in the step of checking a frame in question, a temporal correlation width indicative of a correlation width in a temporal direction is adjusted so as to suppress an influence of changes in the speed of the ultrasonic probe to be given to the extraction results, based on the speed information. In the step of checking a frame in question, it is determined whether the frame in question is the normal frame or the abnormal frame, based only on analyzed data obtained by analyzing the extraction results of cubic higher-order local autocorrelation features from each frame using the predetermined method, and the reference data for determining normality.

In the above-mentioned method, if the predetermined method is a subspace method, and a normal subspace obtained by performing principal component analysis on the extraction results of each frame is stored as the reference data for determining normality in the reference data storage, the step of checking a frame in question includes the steps of calculating a distance, determining a distance, and determining a state. In the step of calculating a distance, a distance between the normal subspace and a subspace obtained by analyzing the extraction results of cubic higher-order local autocorrelation features from each frame is calculated. In the step of determining a distance, it is determined whether or not the distance is a normal distance, based on whether or not the distance exceeds a predefined threshold. In the step of determining a state, it is determined that the frame in question is the normal frame when it is determined in the step of determining a distance that the distance is the normal distance and that the frame in question is the abnormal frame when it is determined in the step of determining a distance that the distance is not the normal distance.

If a one-class SVM (Support Vector Machine) is employed as the predetermined analyzing method, only normal frames are used to define normal classes of normal frames as the reference data for determining normality. In the step of checking a frame in question, it is determined whether or not the frame in question is the normal frame according to whether or not analyzed data of the frame in question fall in the normal classes. The use of this method increases detection accuracy, compared with the subspace method.

BRIEF DESCRIPTION OF DRAWINGS

FIG. 3 is an illustration used to explain a ROC analysis.

FIGS. 12A and 12B illustrate ROC curves for examinee A.

DESCRIPTION OF EMBODIMENTS

Now, embodiments of an ultrasound examination system and an ultrasound examination method of the present invention will be described below in detail with reference to accompanying drawings.

First Embodiment

Figure 1:
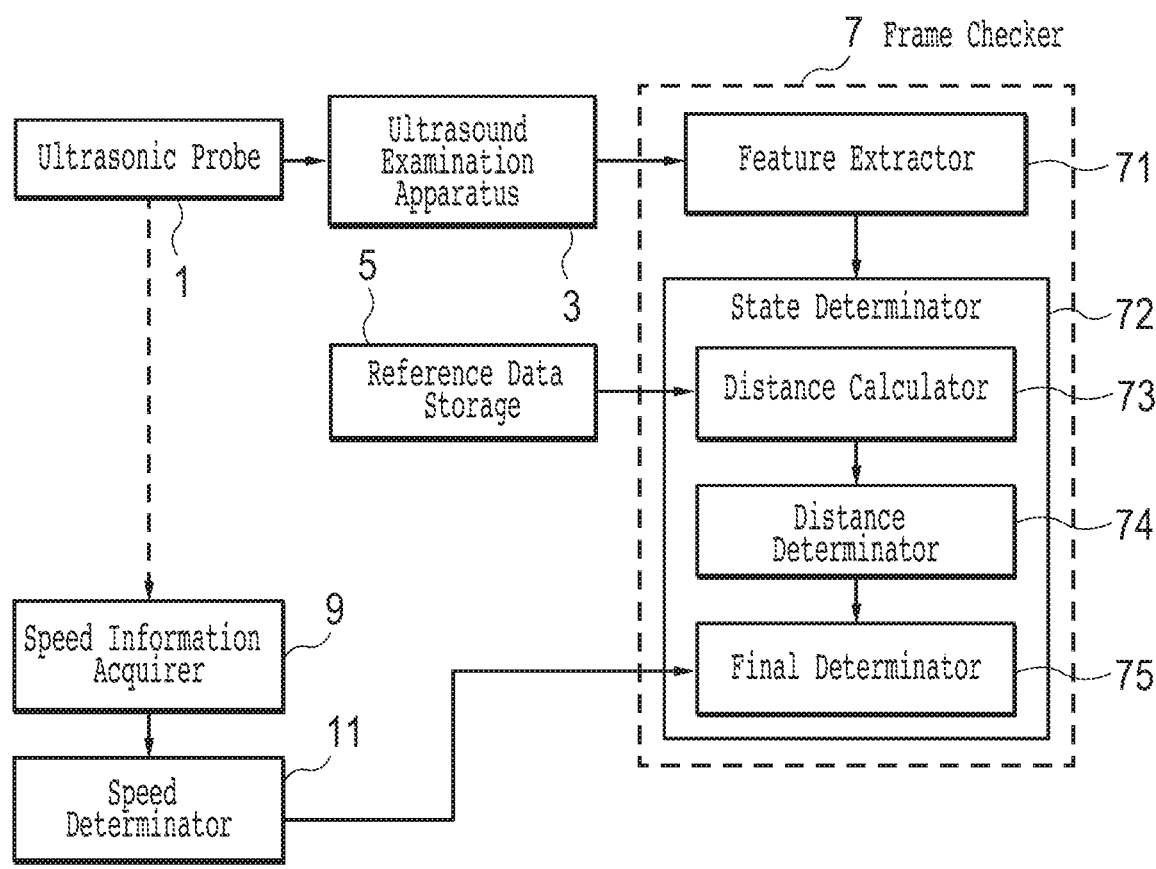
FIG. 1 is a block diagram illustrating the configuration of an ultrasound examination system and an ultrasound examination method according to a first embodiment of the present invention.

FIG. 1 is a block diagram illustrating the configuration of an ultrasound examination system and an ultrasound examination method according to a first embodiment of the present invention. In the first embodiment, it is detected by ultrasound examination whether or not a lesion exists in mammary glands, for example. As described earlier, the ultrasound examination of mammary glands is directed to two types, a tumor and a non-mass image-forming lesion. Since a tumor is depicted or visualized darker than its neighboring tissues, it can be detected by observing static images. On the other hand, it is difficult to detect a non-mass image-forming lesion by observing static images since it is not depicted or visualized in dark shadow. It is, therefore, necessary to grasp regular changes in mammary gland patterns depicted or rendered in a dynamic image and detect a part where the regularity is disturbed. In conventional methods for automatically detecting a mammary gland lesion based on ultrasound images, tumors are targets discoverable from static images only. No methods directed to non-mass image-forming lesions have been developed. Then, in the first embodiment, pattern recognition technology for dynamic images is utilized to enable non-mass image-forming lesions to be automatically detected.

FIG. 1 is a block diagram illustrating the configuration of an ultrasound examination system according to the first embodiment of the present invention. In the ultrasound examination system of the first embodiment, pattern recognition technology of dynamic images is utilized to learn how normal mammary glands change by observing ultrasound images of normal mammary glands, and to detect parts of the mammary glands, which are different from normal mammary glands, as abnormality. An ultrasound system of FIG. 1 is intended to examine whether or not a lesion exists, based on a dynamic image comprised of a plurality of frame arrays that are temporally continuous and are output from an ultrasound examination apparatus 3 with an ultrasonic probe 1 being manipulated. Here, the dynamic image is visualization of a cubic structure and the speed of the ultrasonic probe, based on cross-sectional images of the inside of a human body. The ultrasound examination system comprises a reference data storage 5, a frame checker 7, a speed information acquirer 9, and a speed determinator (determiner) 11.

The reference data storage 5 stores reference data for determining normality that are obtained by learning in advance, specifically by extracting cubic higher-order local autocorrelation features from a plurality of frames that constitute a dynamic image of a human body part where a lesion does not exist as obtained from a reference examinee or an examinee with the ultrasonic probe 1 being manipulated at a speed within a predetermined speed range, and analyzing extraction results by a predetermined analyzing method. An arbitrary method may be employed as the predetermined method. For example, a subspace method and one-class SVM (Support Vector Machine) may be used. In order to grasp the changes in mammary gland pattern from the ultrasound images, cubic higher-order local autocorrelation (CHLAC) features indicative of dynamic image features are used. For details on CHLAC (Cubic Higher-order Local Auto-Correlation) features, refer to "Three-way autocorrelation approach to motion recognition" by Takumi Kobayashi and Nobuyuki Otsu; Pattern Recognition Letters; Volume 30, Issue 3; 1 Feb. 2000; pages 212-221. For details on One-class SVM, refer to "Estimating the support of a high-dimensional distribution" by B. Scholkopf et al.; Neural Computation, 13(7), 2001.

Figure 2A:
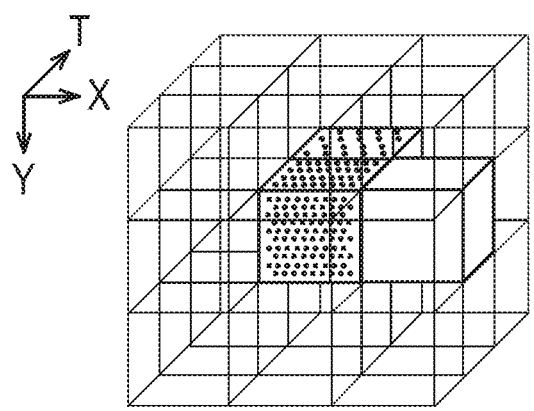
FIG. 2A illustrates an example cubic mask pattern.
Figure 2B:
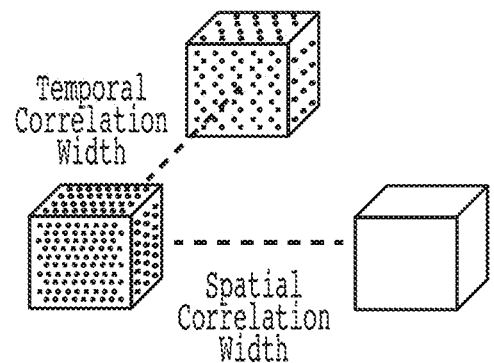
FIG. 2B is an illustration used to explain a spatial correlation width and a temporal correlation width.

In the first embodiment, there are two reasons for using the CHLAC features. The first reason is that the CHLAC features are hardly affected by speckle noise that is included in large quantity in the ultrasound images of mammary glands. Scattered waves are generated in different phases due to a number of reflectors in a living organism that are sufficiently smaller than the wavelength of ultrasonic waves. Out of the scattered waves, "back scattered waves returning to the ultrasonic probe" interfere with other scattered waves, thereby causing a group of small bright spots to appear randomly. The group of small bright spots takes on a mottled or spotty image. This is called speckle pattern or speckle noise (refer to http://us-ism.net/mobile/sub8-S.html). The second reason is that when CHLAC features are used, it is possible to capture the motion and shape of an object depicted or rendered in a dynamic image. As illustrated in FIG. 2A, the CHLAC features are obtained by scanning 279 types of cubic patterns (mask patterns) from each frame of the gray-scaled dynamic image. The CHLAC features are represented as 279-dimensional vector. Here, the value of 279 means the number of independent combinations that are not equivalent to each other when each combination being moved in parallel, out of all combinations of two pixels (three pixels including a target pixel) to be arbitrarily selected from a small region of X×Y×T=3×3×3 centering on the target pixel. Binarized video data is represented as 251-dimensional vector. In the ultrasonographic diagnosis, diagnostic results will not change when the dynamic image is inverted laterally (right and left). The dimension of a vector can be suppressed by means of integration of the features obtained by scanning mask patterns that are equivalent to each other when laterally inverted. Thus, identification accuracy of the subspace method and One-class SVM can be increased. In this case, the vector length is 172 dimensions. As illustrated in FIG. 2B, local or general information can be captured by varying the size of the cubic mask. The size of the cubic mask can be adjusted by varying the spatial correlation width indicative of a correlation width in an X-Y planar direction and the temporal correlation width indicative of a correlation width in the time (t) direction.

However, when the CHLAC features are applied to the ultrasound images of mammary glands, there is a risk that a normal frame may be detected as abnormality, thereby causing over detections. If the CHLAC features considerably change between two consecutive frames, it is not possible to determine whether the considerable changes in mammary gland pattern are due to an influence of a lesion or considerable changes in captured image are due to a large positional change of the ultrasonic probe. This is because the CHLAC features include information on the motion of the ultrasonic probe manipulated by an examiner. Then, in the first embodiment, in addition to abnormality detection based on the CHLAC features, speed information on the moving speed of an ultrasonic probe is used to suppress over detections.

In the first embodiment, the subspace method is applied, as a predetermined analyzing method, to the CHLAC features extracted from ultrasound images of normal mammary glands. A normal subspace is thus calculated as the reference data for determining normality. In the subspace method, a main component vector representative of a normal class is calculated by using main component analysis, and a space formed by the main component vectors is defined as a normal subspace. The number of dimensions for the normal subspace is determined by a threshold $T_{cc}$ for accumulated contribution rate. Namely, base vectors for the subspace are determined as follows. The main component vectors obtained as a result of the main component analysis are lined up in a descending order of corresponding contribution rates (values obtained by dividing the eigenvalue of each eigenvector by the total eigenvalues of all eigenvectors). When adding up the contribution rates in order, the main component vectors just before the total value of the contribution rates exceeds the threshold $T_{cc}$ are employed as base vectors for the subspace. Therefore, setting a lower value to the threshold $T_{cc}$ will decrease the dimension of the subspace. Conversely, setting a higher value to the threshold $T_{cc}$ will increase the dimension of the subspace. Instead of using the threshold $T_{cc}$, the number of dimensions for the subspace may directly be specified.

To optimize the threshold $T_{cc}$ for defining the number of dimensions for the normal subspace, an AUC value, which is one of the indices in ROC analysis, is utilized. The AUC (Area Under the Curve) value means an area under the ROC curve. It is one of the performance indices for a classifier, and takes a numeric value of 0 (zero) to 1 (one). An area (AUC value) is 1 when full classification is possible. It is 0.5 for random classification. An arbitrary value is set to the threshold $T_{cc}$ for defining the number of dimensions for the normal subspace. The true positive rate (probability that examination indicates positivity for patients) and the false positive rate (probability that examination indicates positivity for healthy people) are calculated, varying the threshold $T_{NA}$ for identifying normality and abnormality. Thus, a ROC curve is depicted by plotting on a two-dimensional graph with the false positive rate as a lateral axis and the true positive rate as a longitudinal axis. Details on $T_{NA}$ will be described later. A plurality of ROC curves can be obtained by varying the threshold $T_{cc}$ from a predetermined minimum value to a predetermined maximum value. A threshold value $T_{cc}$ that takes the maximum AUC value on these ROC curves is employed as a threshold for defining the number of dimensions for the normal subspace.

The speed information acquirer 9 acquires speed information on a speed of the ultrasonic probe 1 manipulated by the examiner in respect of each frame. Information on the position and posture of the ultrasonic probe 1 can be obtained, for example, by mounting a magnetic field position sensor inside the ultrasonic probe 1.

The speed determinator 11 determines that the speed of the ultrasonic probe 1, which has been obtained from the speed information acquired by the speed information acquirer 9, is a normal speed when the speed of the ultrasonic probe 1 does not exceed a threshold $T_s$ predefined with reference to a speed in the predetermined speed range when a dynamic image has been acquired by learning in advance. Here, a predefined threshold $T_s$ used in the speed determinator is a threshold for suppressing over detections due to an influence of the scanning speed of the ultrasonic probe 1. The threshold $T_s$ is represented by an expression of $T_s = u + k \times \sigma$ where u stands for an average moving speed of the ultrasonic probe in learned dynamic images of mammary glands, $\sigma$ for the standard deviation of the average moving speed, and k for a parameter determined by an experiment. Generally, the parameter (k) takes a value of $1 \leq k \leq 3$. A value of the threshold $T_s$ specifically defined by the expression is larger than 0.

The frame checker 7 includes a feature extractor 71 and a state determinator (determiner) 72. The feature extractor 71 extracts cubic higher-order local auto correlation features from each of a plurality of frames that constitute a dynamic image of a human body part as obtained from the ultrasound examination apparatus 3 while an examiner manipulates the ultrasonic probe 1 on the examinee. The state determinator 72 determines whether a frame in question is a normal frame not containing the lesion or an abnormal frame containing the lesion, based on extraction results of cubic higher-order local autocorrelation features from each frame and the reference data for determining normality stored in the reference data storage 5.

The feature extractor 71 extracts cubic higher-order local autocorrelation features from each of a plurality of frames that constitute a dynamic image of a human body part as obtained from the ultrasound examination apparatus 3, as with when acquiring the reference data for determining normality from the reference data storage 5 as mentioned above.

The state determinator 72 includes a distance calculator 73, a distance determinator (determiner) 74, and a final determinator (determiner) 75. The distance calculator 73 calculates a distance between the extraction results of cubic higher-order local autocorrelation features from each frame and the normal subspace obtained from analysis by the subspace method. The distance determinator 74 determines whether or not the distance is a normal distance, based on whether or not the distance exceeds a predefined threshold TNA. The final determinator 75 determines that the frame in question is the normal frame when the distance determinator 74 determines that the distance is the normal distance and when the distance determinator 74 determines that the distance is not the normal distance and the speed determinator 11 determines that the speed is not the normal speed. The final determinator 75 also determines that the frame in question is the abnormal frame when the distance determinator 74 determines that the distance is not the normal distance and the speed determinator 11 determines that the speed is the normal speed.

The threshold TNA used in the distance determinator 74 to determining normality or abnormality is determined by ROC (Receiver Operating Characteristic) analysis. An ROC curve obtained from the ROC analysis is a plotting trajectory on a two-dimensional graph with the false positive rate (probability that examination indicates positivity for healthy people) as the lateral axis and the true positive rate (probability that examination indicates positivity for patients) as the longitudinal axis (refer to (http://oku.edu.mie-u.ac.jp/~okumura/stat/ROC.html). As the ROC curve goes up leftward, in other words, the closer the true positive rate is to 1 and the false positive rate is to 0, the higher the classifying performance is indicated. FIG. 3 shows an example ROC curve. In this example, the respective true and false rates with a threshold SH in two-dimensional graphs illustrated in the frames A, B, and C are plotted on the ROC curve. In the first embodiment, a threshold corresponding to the point of intersection of the ROC curve and straight line L having an inclination of 45 degrees is employed as an optimal threshold TNA. Those frames determined as abnormal by using the optimal threshold TNA may include over detections due to changes in moving speed of the ultrasonic probe. Then, in the first embodiment, for those frames in which the distance is determined as abnormal by the distance determinator 74, if the speed determinator 11 determines that the moving speed of the ultrasonic probe 1 exceeds the threshold Ts defined in advance, over detection is assumed. Then, the final determinator 75 finally determines that only those frames in which the moving speed is equal to or lower than the threshold Ts are abnormal frames. As a result, according to the present invention, the over detection rate can significantly be reduced. The frame checker 7 may be implemented using a computer.

[Description of the Flowchart of Implementing the First Embodiment]

Figure 4:
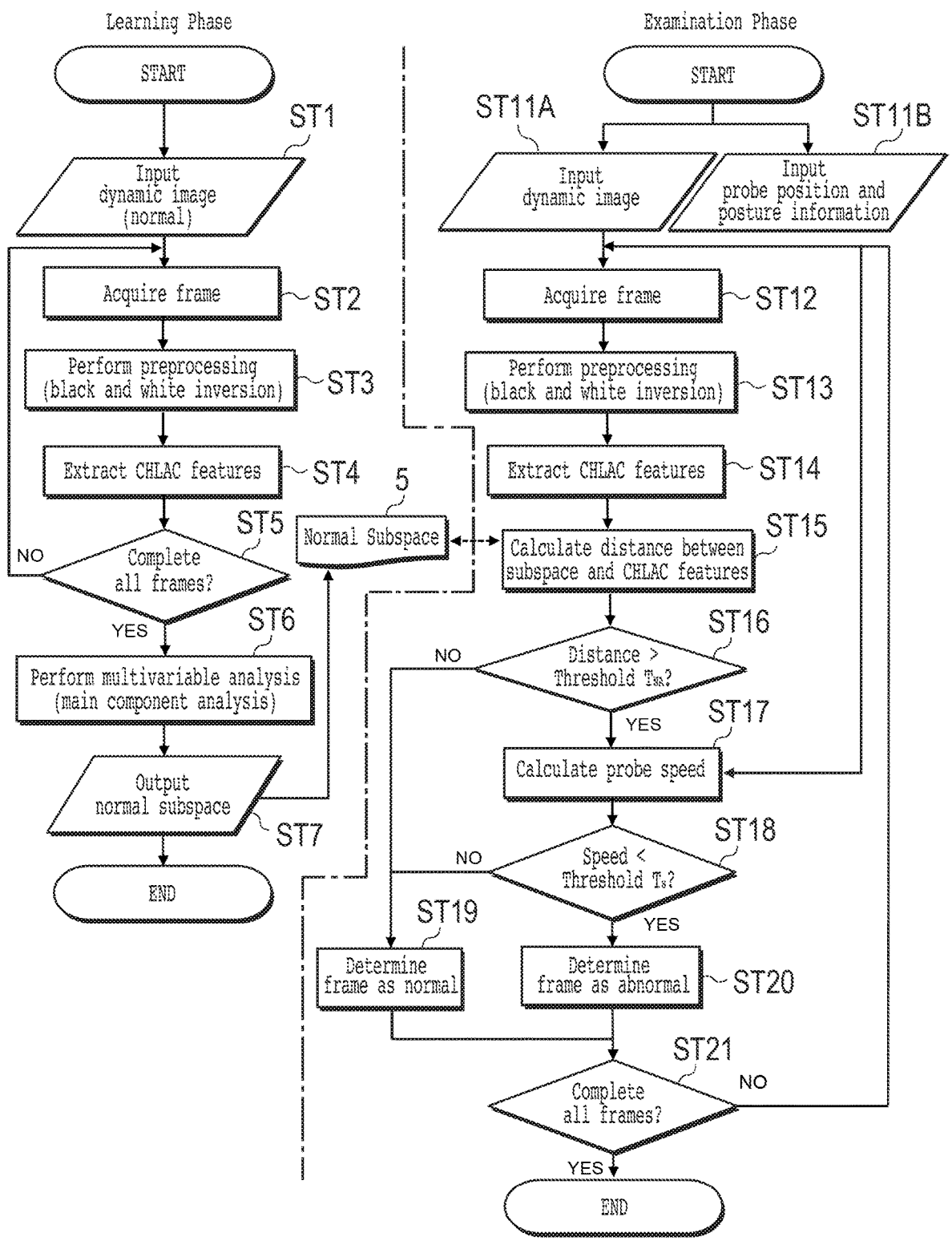
FIG. 4 is a flowchart illustrating an algorithm of software for implementing the embodiment of FIG. 1 using a computer.

FIG. 4 is a flowchart illustrating an algorithm of software for implementing the first embodiment. The algorithm illustrated in the flowchart of FIG. 4 includes an algorithm of software in the learning phase and an algorithm in the examination phase. In the learning phase, reference data for determining normality are created and stored in the reference data storage 5 as described earlier. In the first embodiment, the subspace method is employed as the analyzing method and normal subspaces are stored as reference data for determining normality in the reference data storage 5. In steps ST1 and ST2, a plurality of frames that constitute a dynamic image of a human body part where a lesion does not exist are obtained from a reference examinee or an examinee with an ultrasonic probe 1 being manipulated. The cubic higher-order local autocorrelation (CHLAC) features, which will be described later, show strong reactions with white portions with high brightness in the image. Abnormalities such as tumors are depicted or rendered dark with low brightness in the ultrasound images. In the first embodiment, to eliminate mismatching of the depictions as described above, black and white inversion (monochrome inversion) of the image is performed as pre-processing in step ST3. The lesions can be furthermore highlighted by emphasizing contrast in addition to the black and white inversion. Alternatively, pre-processing time can be saved by not performing black and white inversion, thereby increasing the processing speed. Then, in step ST4, cubic higher-order local autocorrelation (CHLAC) features are extracted from the acquired frames. These steps are performed for all the acquired frames (in step ST5). After that, once cubic higher-order local autocorrelation (CHLAC) features have been extracted in respect of all the frames, a predetermined analyzing method (the main component analysis for the subspace method) is applied to extraction results (in step ST6) and the thus obtained normal subspaces are stored as the reference data for determining normality in the reference data storage 5 (in step ST7). As described above, the learning step is constituted from steps ST 1 to ST7.

In the examination phase, a plurality of frames that have been obtained from the ultrasound examination apparatus and constitute a dynamic image of a human body part of an examinee are entered (in steps ST11A and ST12). The information on the position and posture of the ultrasonic probe is detected by a magnetic position sensor, for example, and is entered. After pre-processing (black and white inversion) has been performed on the frames that have been obtained from the ultrasound examination apparatus while the examiner manipulates the ultrasonic probe on the examinee and that constitute the dynamic image of the human body part (in step ST13), the cubic higher-order local autocorrelation (CHLAC) features are extracted from each frame (in step ST14: the step of extracting features). If contrast emphasis or the like has been performed in addition to the black and white inversion in the learning phase, or if the pre-processing has not been performed at all, the like processing is performed or pre-processing is not performed also in the examination phase.

Next, a distance is calculated between extraction results of cubic higher-order local autocorrelation features from each frame and the reference data for determining normality (normal subspaces) that are analyzed data obtained by using the predetermined method to analyze the extraction results of cubic higher-order local autocorrelation features from each frame of the dynamic image for learning in the learning phase (in step ST15: the step of calculating a distance). It is then determined whether or not thus calculated distance is a normal distance according to whether or not the calculated distance exceeds the predefined threshold $T_{NA}$ (in step ST 16: the step of determining a distance). If it is determined that the distance is a normal distance, the process goes to step ST19 where it is determined that the frame in question is a normal frame. If the distance exceeds the threshold $T_{NA}$, the process goes to step ST17. In step ST17 (the step of acquiring speed information), the speed of the ultrasonic probe is calculated and it is determined whether the speed of the ultrasonic probe exceeds the predetermined threshold $T_s$ (in step ST18: the step of determining a speed). If the speed of the ultrasonic probe exceeds the predefined threshold $T_s$, it is determined that the speed is not a normal speed. Even though the frame has been determined as abnormal in the step of determining a distance as described above, that frame is determined as a normal frame and the process goes to step ST19. If the speed of the ultrasonic probe does not exceed the predefined threshold $T_s$, the speed is determined as a normal speed and the process goes to step ST20 where the frame in question is determined as an abnormal frame. Then in step ST21, once it is determined that all the frames have been examined, the examination phase is ended. The step of determining a state is constituted from steps ST19 to ST21. The step of checking a frame in question is constituted from steps ST15 to ST21.

[Experiment]

To confirm the effects of the embodiment described so far, an abnormality detection experiment was performed on an examinee who had been examined and determined as having a non-mass image-forming lesion.

Figure 5:
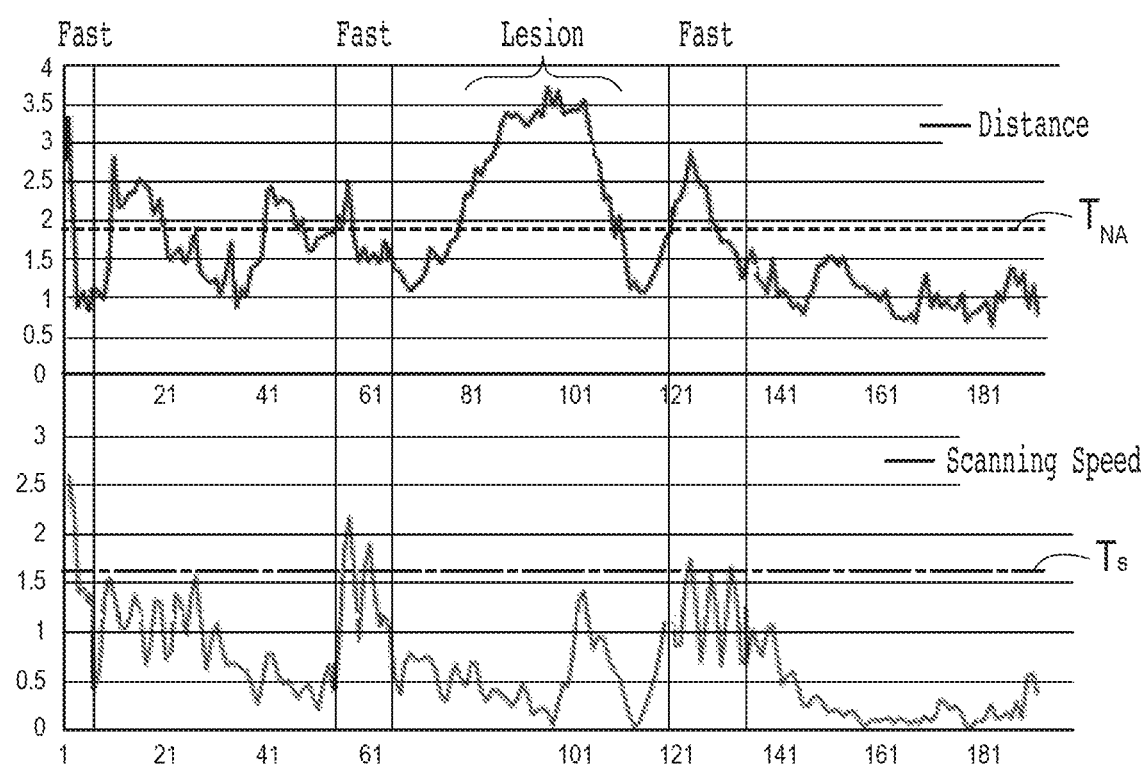
FIG. 5 is a graph illustrating experiment results of the first embodiment.

In the experiment, it was confirmed, according to the first embodiment, whether or not over detections could be suppressed at human body parts where the scanning speed of the ultrasonic probe was increased. In the experiment, parameter k was set to 1.8 (k=1.8) in the speed threshold $T_s$ (=u+k×σ). The experiment results are shown in FIG. 5. The graph illustrated in the upper part of FIG. 5 represents the distance to the normal subspace, and the graph illustrated in the lower part of FIG. 5 represents the scanning speed of the ultrasonic probe. For the segments where the scanning speed was increased (the speed exceeded the threshold $T_s$ in the lower graph), such segments were indicated with "Fast" in FIG. 5. In the segments where the scanning speed was increased, it can be known that the distance became longer due to the influence of the increased scanning speed. Although the frames surrounded by boundaries were excessively detected as abnormal frames only with the use of the threshold $T_{NA}$ for the distance to the normal subspace, the use of the threshold $T_s$ for scanning speed of the ultrasonic probe could suppress over detections due to the scanning speed.

Second Embodiment

Figure 6:
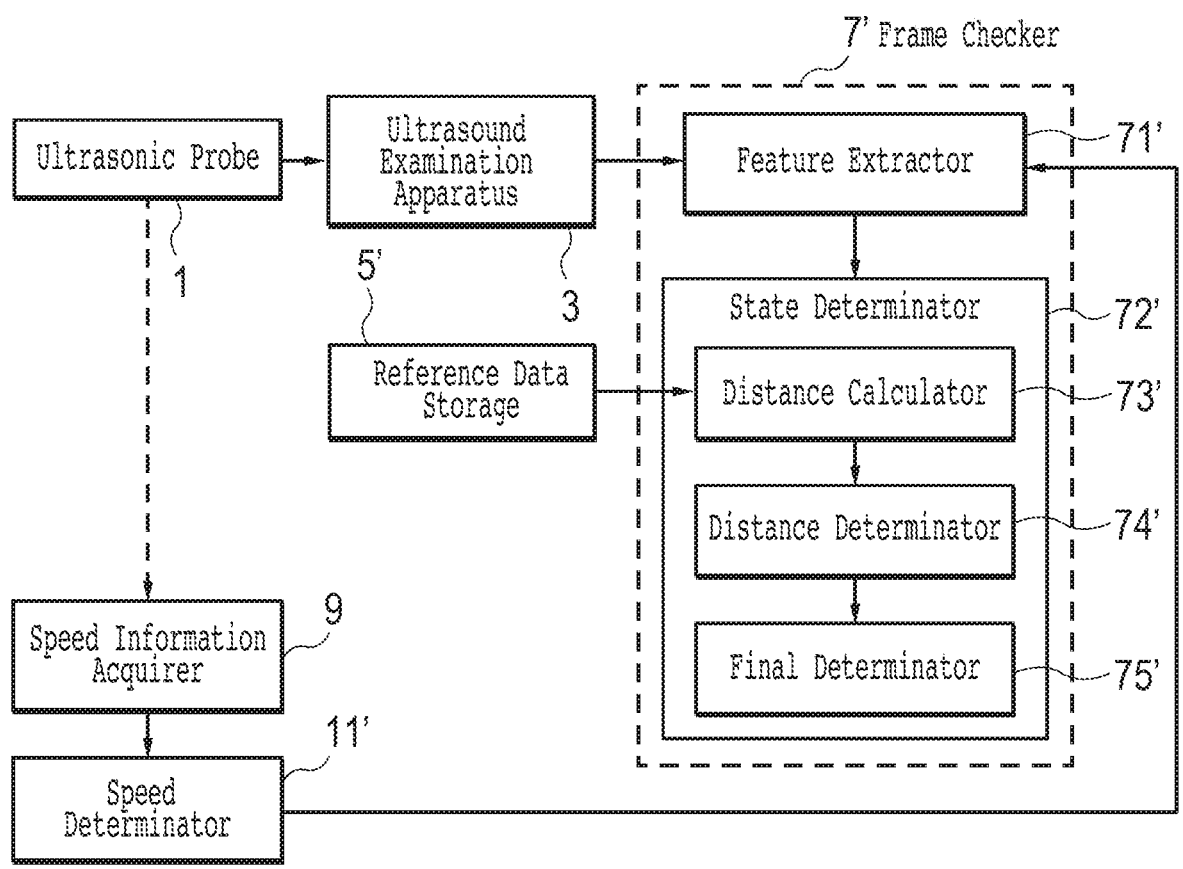
FIG. 6 is a block diagram illustrating the configuration of an ultrasound examination system and an ultrasound examination method according to a second embodiment of the present invention.
Figure 7:
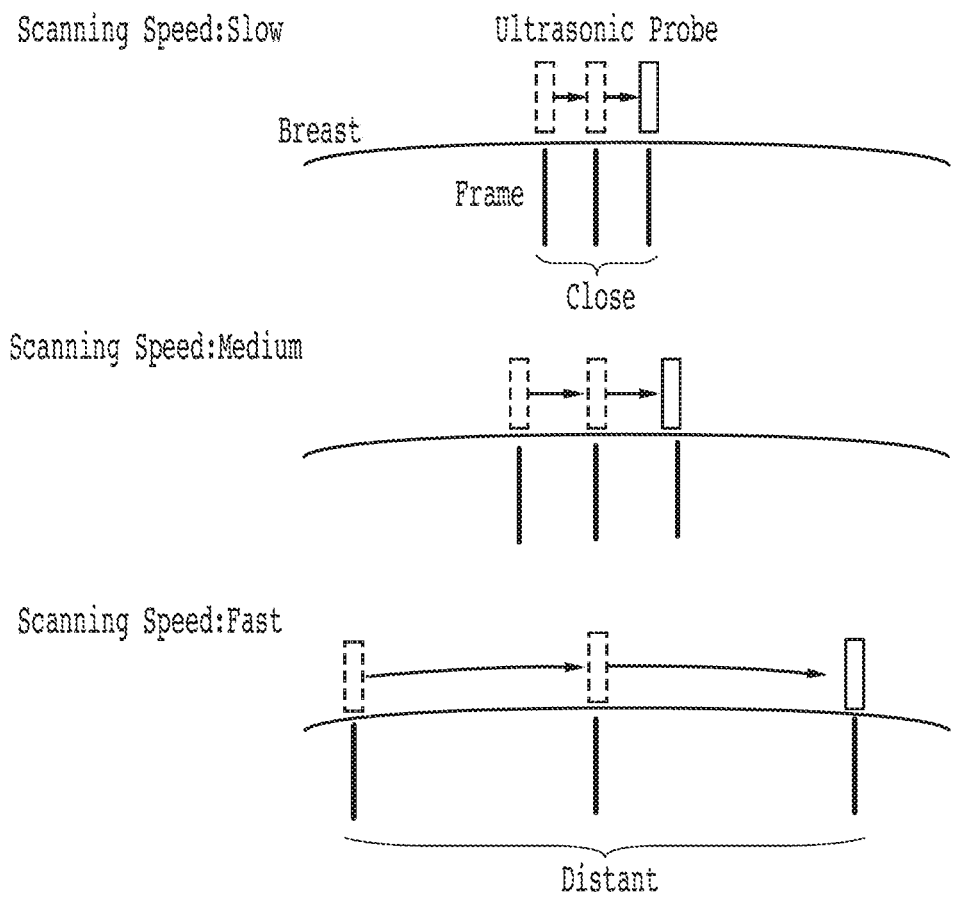
FIG. 7 illustrates the relationship between the scanning speed of an ultrasonic probe and the positions at which frames are acquired.
Figure 8:
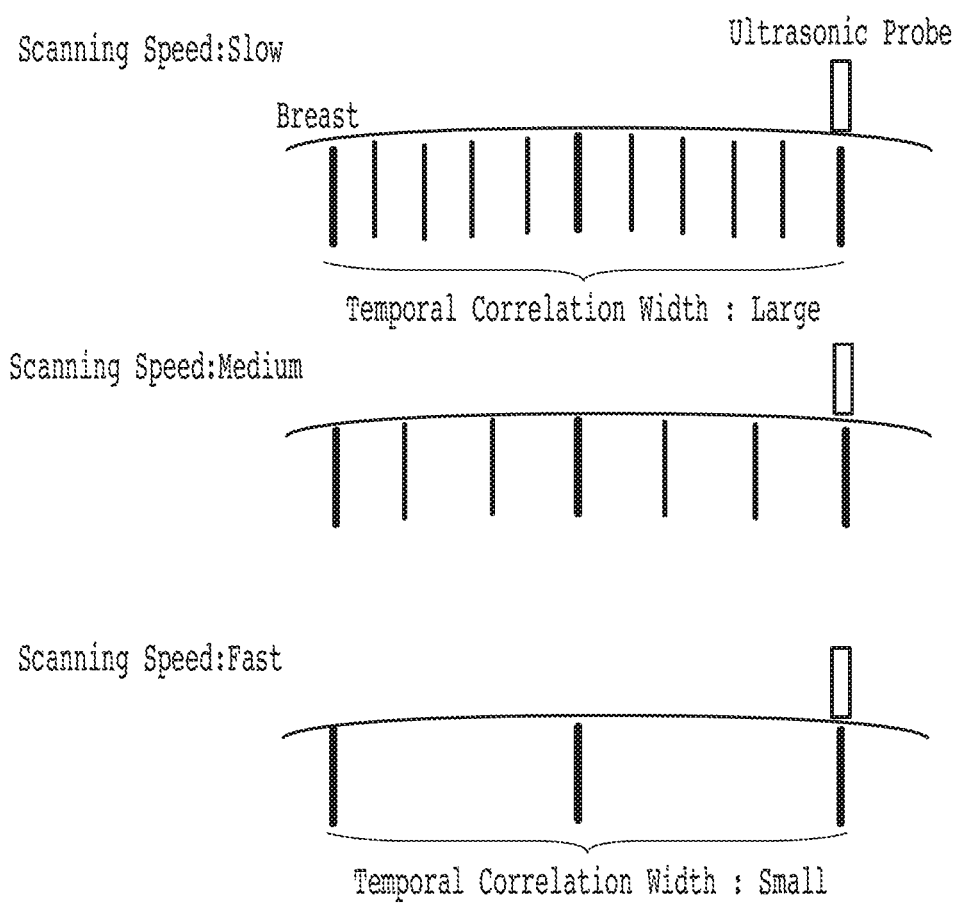
FIG. 8 is an illustration used to explain a frame in question in CHLAC (cubic higher-order local autocorrelation) features according to the second embodiment.

FIG. 6 is a block diagram illustrating the configuration of an ultrasound examination system and an ultrasound examination method according to a second embodiment of the present invention. The structural elements of a block diagram of FIG. 6 are affixed with the same reference numerals as the counterpart elements of the first embodiment illustrated in a block diagram of FIG. 1 and the explanation thereof is omitted. The second embodiment is also directed to example ultrasound examination of a lesion in mammary glands. In the second embodiment, the cubic higher-order local autocorrelation (CHLAC) features are extracted by appropriately varying the temporal correlation width according to the scanning speed of the ultrasonic probe 1. If the cubic higher-order local autocorrelation (CHLAC) features are applied to the ultrasound images of mammary glands, the performance of abnormality detection is affected by the motion of the ultrasonic probe 1. As illustrated in FIG. 7, for example, if the scanning speed of the ultrasonic probe 1 is fast, adjacent frames are captured at more distant positions than when the scanning speed is slow. For this reason, although the same mammary glands are captured, if the scanning speed is different, the mammary glands are represented by different cubic higher-order local autocorrelation (CHLAC) features. In the second embodiment, as illustrated in FIG. 8, the cubic higher-order local autocorrelation (CHLAC) features are extracted from the frames that have been captured at equidistant intervals by varying the temporal correlation width (FIG. 2) according to the scanning speed of the ultrasonic probe 1 in order to alleviate the above-mentioned influence.

Figure 9:
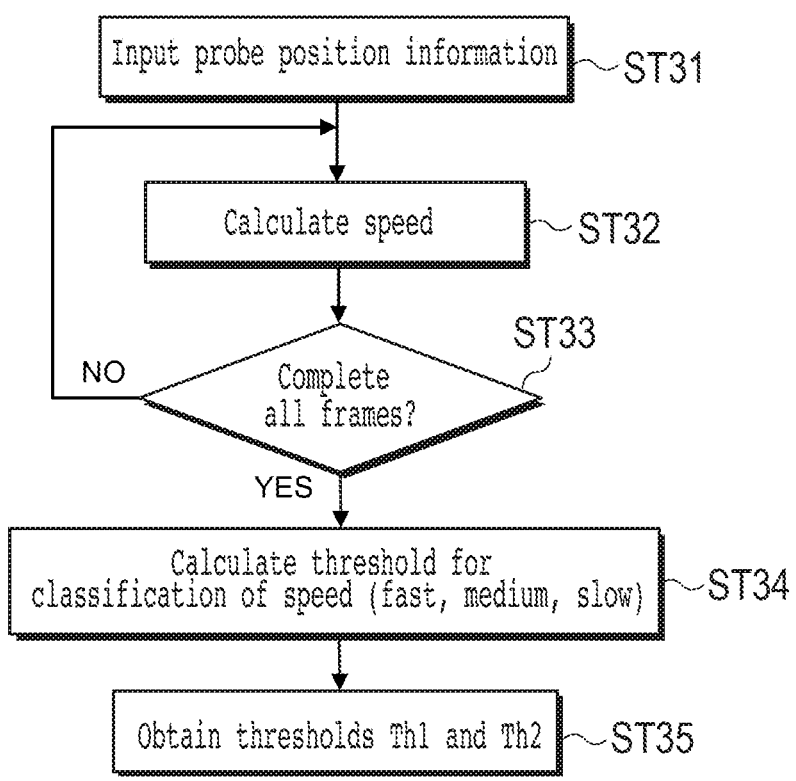
FIG. 9 is a flowchart illustrating an algorithm for implementing pre-learning.

In the second embodiment, pre-learning is performed before entry into the learning phase for the purpose of calculating thresholds Th1 and Th2 for classifying the speed into three levels {fast, medium, slow}. FIG. 9 is a flowchart illustrating an algorithm for implementing pre-learning. First, pre-learning is performed to calculate a speed from a plurality of frames that constitute a dynamic image of a human body part where a lesion does not exist as obtained from a reference examinee or an examinee with an ultrasonic probe being manipulated by an operator (in steps ST31 to ST33). Then, the thresholds Th1 and Th2 are determined to classify the calculated speeds into three levels, fast, medium, and slow (in steps ST34 and ST35). The pre-learning is preferably performed for each operator engaged in the examination. A reference data storage 5' stores reference date for determining normality that are obtained by extracting cubic higher-order local autocorrelation features from a plurality of frames that constitute a dynamic image of a human body part where a lesion does not exist as obtained from the reference examinee or the examinee with the ultrasonic probe 1 being manipulated while appropriately varying the temporal correlation width using the thresholds Th1 and Th2, and analyzing extraction results by a predetermined analyzing method. Specifically, the scanning speed of the ultrasonic probe 1 is acquired for quantization in order to adjust the temporal correlation width of the cubic higher-order local autocorrelation (CHLAC) features. Position information for each frame is acquired from a magnetic position sensor or the like mounted on the ultrasonic probe, and the scanning speed is calculated between the frames. The calculated scanning speeds are quantized into three levels [slow, medium, fast]. As a method of quantization, the minimum value to the maximum value of the scanning speed of the ultrasonic probe in already captured ultrasound images of mammary glands are classified into three segments [slow, medium, fast in an ascending order] and it is determined which segment the speeds should be classified into. Segment classification may be uneven. To appropriately vary the temporal correlation width of the cubic higher-order local autocorrelation (CHLAC) features according to the scanning speed, the cubic higher-order local autocorrelation (CHLAC) features are extracted by changing the temporal correlation width for the three quantized speeds, specifically, T # large for slow speeds, T # medium for medium speeds, and T # small for fast speeds. The temporal correlation width may arbitrarily be set. Generally, the relationship of T # small<T # medium<T # large is satisfied. With this setting, the temporal correlation width is adjusted in a weakly monotonically decreasing manner according to the magnitude of scanning speed. In an experiment on a computer, following the flowchart illustrated in FIGS. 10 and 11, value settings were T # large=5, T # medium=3, and T # small=1. Then, the subspace method is applied to the cubic higher-order local autocorrelation (CHLAC) features extracted from ultrasound images of normal mammary glands, and normal subspaces are calculated. In the subspace method, main component analysis is performed to calculate main component vectors representative of normal classes. A space formed by the main component vectors is defined as a normal subspace. The method of determining a normal subspace is the same as the one in the first embodiment and the explanation thereof is omitted.

The thresholds Th1 and Th2 are stored in a speed determinator (determiner) 11'. A feature extractor 71' in a frame checker 7' selects a temporal correlation width corresponding to the speed of the ultrasonic probe within three speed threshold ranges defined by the thresholds Th1 and Th2 that stepwisely increase in value, based on the extraction results obtained from the speed determinator 11'. A state determinator (determiner) 72' in the frame checker 7' determines whether the frame in question is a normal frame or an abnormal frame, based on the extraction results of cubic higher-order local autocorrelation (CHLAC) features from each frame and the reference data for determining normality. The operations of a distance calculator 73', a distance determinator (determiner) 74', and a final determinator (determiner) 75' are the same as those of the distance calculator 73, the distance determinator 74, and the final determinator 75 in the first embodiment. The feature extractor 71' extracts cubic higher-order local autocorrelation (CHLAC) features from the ultrasound images of mammary glands under examination with the temporal correlation width being automatically adjusted based on the scanning speed of the ultrasonic probe. Next, the distance calculator 73' calculates a distance between the extracted cubic higher-order local autocorrelation (CHLAC) features and the normal subspace prepared in the learning phase. The distance determinator 74' and the final determinator 75' determine that the frame in question is an abnormal frame when the distance exceeds a threshold defined in the same manner as the first embodiment.

According to the second embodiment, the temporal correlation width representative of a correlation width in a temporal is adjusted so as to suppress an influence of changes in speed of the ultrasonic probe to be given to the extraction results. Therefore, it is possible to suppress over detections due to too fast speeds of the ultrasonic probe. Unlike the first embodiment in which the speed of the ultrasonic probe is a direct determination standard, the erroneous detection rate of abnormal frames can considerably be reduced.

[Flowchart of Implementing the Second Embodiment]

Figure 10:
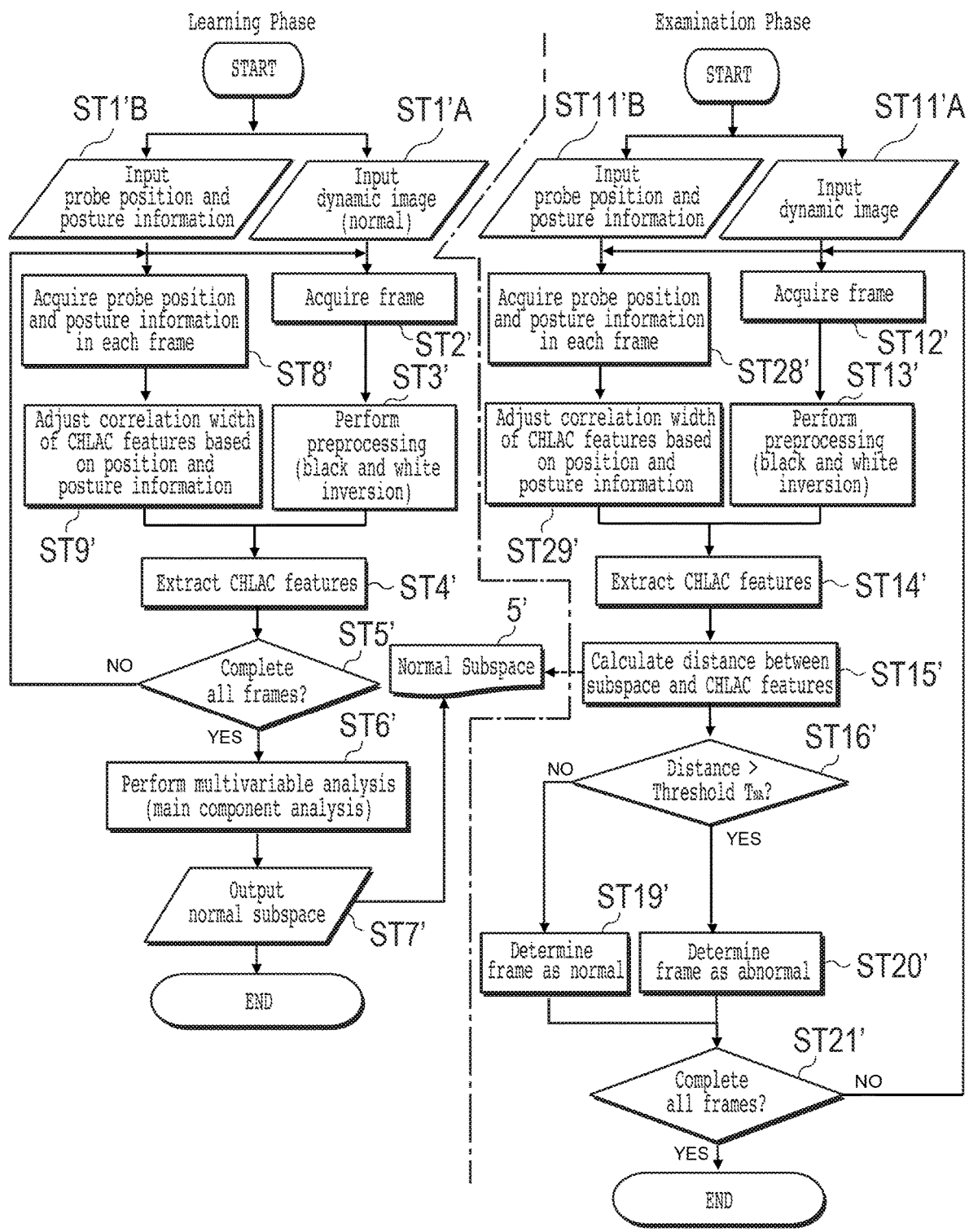
FIG. 10 is a flowchart illustrating an algorithm of software for implementing the second embodiment of FIG. 6 using a computer.

FIG. 10 is a flowchart illustrating an algorithm of software for implementing the second embodiment of FIG. 6 using a computer. The algorithm illustrated in FIG. 10 includes a software algorithm in the learning phase and an algorithm in the examination phase. In the learning phase, reference data for determining normality are created and stored in the reference data storage 5' as described earlier. In the second embodiment, the subspace method is employed as an analyzing method and normal subspaces are stored as reference data for determining normality in the reference data storage 5'. Insteps ST1' and ST2', a plurality of frames that constitute a dynamic image of a human body part where a lesion does not exist as obtained from a reference examinee or an examinee with an ultrasonic probe being manipulated. In steps ST1'A and ST2', a plurality of frames that constitute a dynamic image of a human body part where a lesion does not exists as obtained from the reference examinee or the examinee while the operator manipulates the ultrasonic probe 1. In step ST3', black and white inversion of the images is performed as pre-processing. The lesions can be furthermore highlighted by emphasizing contrast in addition to the black and white inversion. Alternatively, pre-processing time can be saved by not performing black and white inversion, thereby increasing the processing speed. In step ST1'B, information on the position and posture of the ultrasonic probe is acquired using a magnetic position sensor mounted on the ultrasonic probe. In step ST8', the information on the position and posture of the ultrasonic probe in each frame is acquired.

Figure 11:
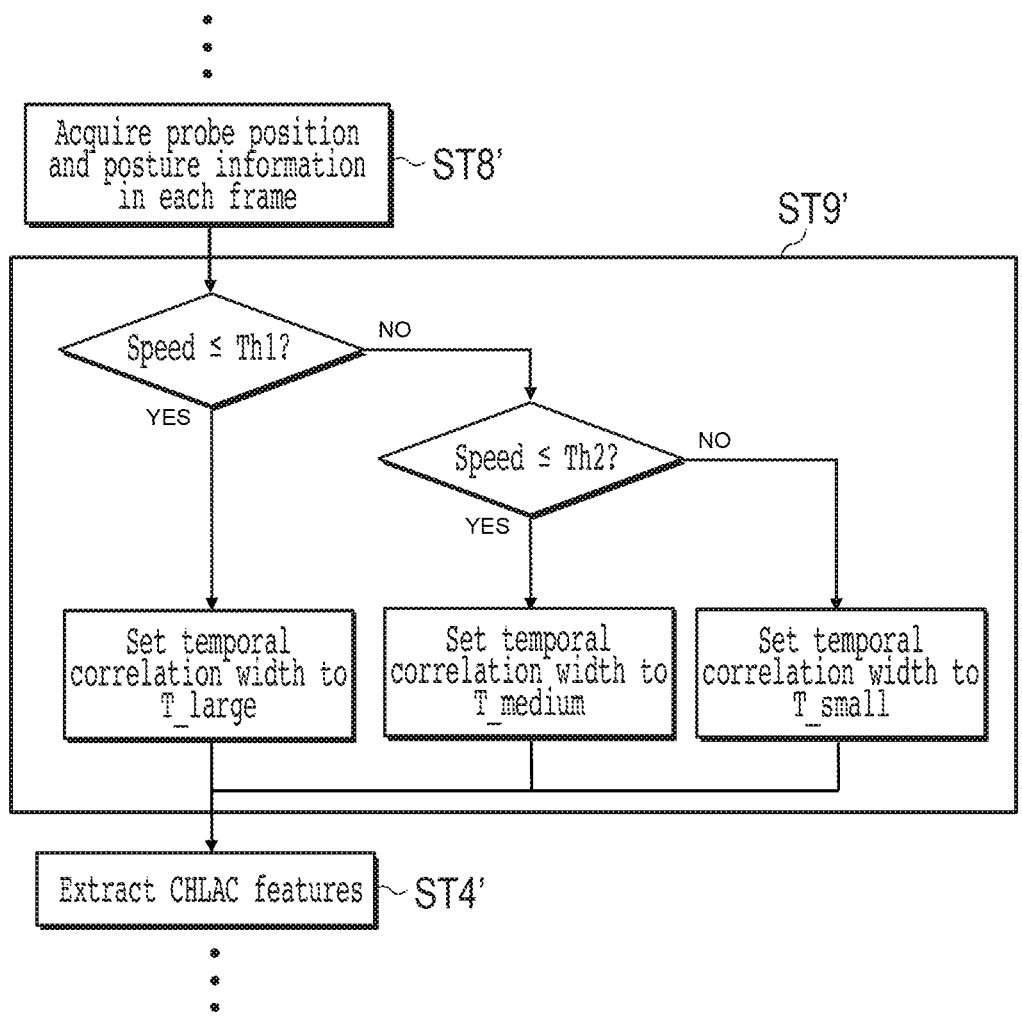
FIG. 11 illustrates example details of step ST9'.

In step ST9', the scanning speed of the ultrasonic probe in each frame is calculated, based on the position and posture information to appropriately adjust the temporal correlation width of the cubic higher-order local autocorrelation (CHLAC) features within a predefined speed threshold range based on the above-mentioned thresholds Th1 and Th2. FIG. 11 illustrates example details of step ST9'. The thresholds Th1 and Th2 are used to quantize calculated speeds into three levels [slow, medium fast]. In step ST9', when determining the thresholds Th1 and Th2, the minimum value to the maximum value of the scanning speed of the ultrasonic probe in already captured ultrasound images of mammary glands are classified evenly into three segments [slow, medium, fast in an ascending order] and it is determined which segment the speeds should be classified into. The temporal correlation width is varied relative to the three quantized speeds as follows: T # large for slow speeds, T # medium for medium speeds, and T # small for fast speeds.

In step 4', cubic higher-order local autocorrelation (CHLAC) features are extracted from each frame by using the temporal correlation width determined in step ST9'. These steps are performed for all the acquired frames (in step ST5'). After that, once cubic higher-order local autocorrelation (CHLAC) features have been extracted in respect of all the frames, a predetermined analyzing method (the main component analysis for the subspace method: step ST6') is applied to extraction results and the thus obtained normal subspaces are stored as the reference data for determining normality in the reference data storage 5' (in step ST7'). Thus, the learning step is constituted from steps ST 1' to ST7'.

In the examination phase, a plurality of frames that constitute a dynamic image of a human body part as obtained from the examinee with an ultrasonic probe being manipulated 1 by the operator in steps ST 11' and 12'. In step 13', black and white inversion of the images is performed as pre-processing. If contrast emphasis or the like has been performed in addition to the black and white inversion in the learning phase, or if the pre-processing has not been performed at all, the like processing is performed or pre-processing is not performed also in the examination phase. In step ST11'B, the information on the position and posture of the ultrasonic probe is acquired by using a magnetic position sensor. In step ST28', the information on the position and posture of the ultrasonic probe in each frame is acquired.

In step ST29', the scanning speed of the ultrasonic probe in each frame is calculated based on the position and posture information, and the temporal correlation width of the cubic higher-order local autocorrelation (CHLAC) features is appropriately adjusted with a speed threshold range determined using the above-mentioned thresholds Th1 and Th2. In step ST29', like step ST9' illustrated in FIG. 11, it is determined which segment the acquired speeds should be classified into. The temporal correlation width is varied relative to the three quantized speeds as follows: T # large for slow speeds, T # medium for medium speeds, and T # small for fast speeds. Step ST29' constitutes a part of the steps of acquiring speed information and checking a frame in question In step ST14' (the step of extracting features), the cubic higher-order local autocorrelation (CHLAC) features are extracted from each frame by using the temporal correlation width determined in step ST29'. Next, a distance is calculated between extraction results of cubic higher-order local autocorrelation features from each frame and the reference data for determining normality (normal subspaces) (in step ST15': the step of calculating a distance). It is then determined whether or not thus calculated distance is a normal distance according to whether or not the calculated distance exceeds the predefined threshold $T_{NA}$ (in step ST 16': the step of determining a distance). If it is determined the distance is a normal distance, the process goes to step ST19' where it is determined that the frame in question is a normal frame. If the distance exceeds the threshold $T_{NA}$, the process goes to step ST20' where it is determined that the frame in question is an abnormal frame. Thus, determination of normal and abnormal frames can be made without being affected by the scanning speed of the ultrasonic probe. In step ST21', once it is determined that all the frames have been examined, the examination phase is ended. The step of determining a state is constituted from steps ST19' to ST21'. The step of checking a frame in question is constituted from steps ST15' to ST21'.

[One-Class SVM as an Analyzing Method]

If one-class SVM (Support Vector Machine) is employed as a predetermined analyzing method, the one-class SVM is applied to the cubic higher-order local autocorrelation (CHLAC) features extracted from ultrasound images of normal mammary glands to calculate a normal class. In the one-class SVM, a method called kernel method capable of discovering data structure is utilized to estimate a region where learning data exist in quantity and to calculate a boundary plane (hyperplane) that distinguish a region (normal class) where the learning data exist in quantity and a region where the learning data do not exist. In the examination phase, it is determined whether the frame in question is a normal frame or an abnormal frame according to whether or not the cubic higher-order local autocorrelation (CHLAC) features extracted from the ultrasound images of mammary glands under examination fall into the normal class calculated in the learning phase.

[Experiment]

To confirm the effects of the second embodiment described so far, an abnormality detection experiment was performed in respect of two examinees A and B. Examinee A had been examined and determined as having a tumor. Examinee B had been examined and determined as having a non-mass image-forming lesion.

Experiment Method (Subspace Method as an Analyzing Method)

In the experiment, in order to verify the validity of extraction of cubic higher-order local autocorrelation (CHLAC) features while varying the temporal correlation width according to the scanning speed of the ultrasonic probe, the ROC curves in the following two cases were compared: the temporal correlation width of cubic higher-order local autocorrelation (CHLAC) features was fixed; and the temporal correlation width of cubic higher-order local autocorrelation (CHLAC) features was varied according to the second embodiment as described earlier. The temporal correlation width was set to [T # large=5, T # medium=3, T # small=1] corresponding to the scanning speeds [slow, medium, fast]. The threshold $T_{cc}$ for defining an optimal number of dimensions of the normal subspace was set to six different values [0.9, 0.99, 0.999, 0.9999, 0.99999, 0.999999] and a value of the threshold when the AUC value was the largest was employed.

Experiment Results (Subspace Method as an Analyzing Method)

Figure 13A:
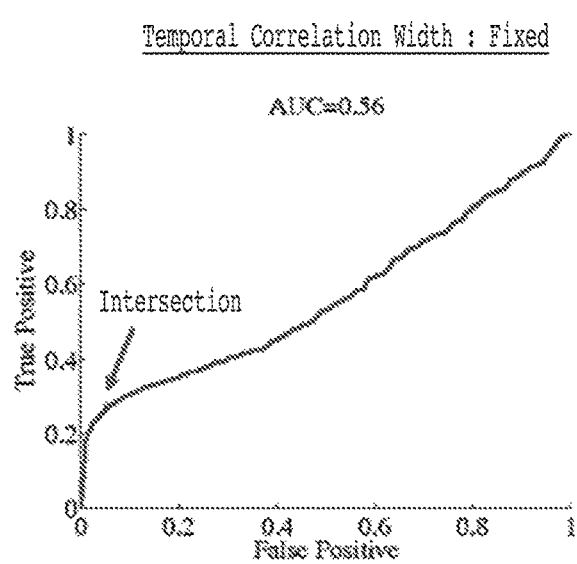
FIGS. 13A and 13B illustrate ROC curves for examinee B.
Figure 13B:
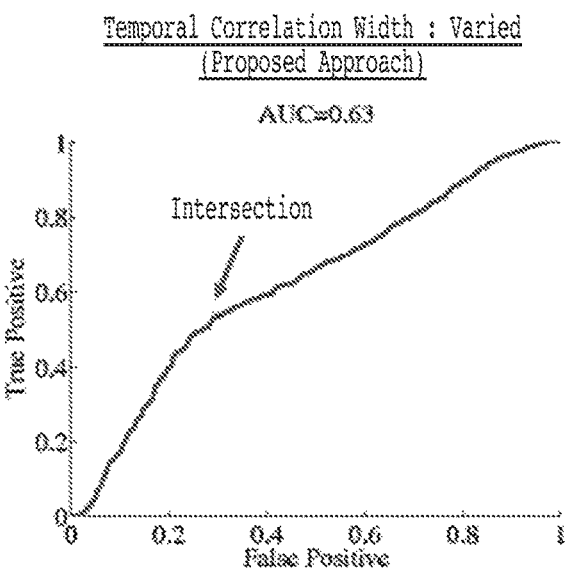

FIGS. 12A and 12B illustrate ROC curves for examinee A. FIGS. 13A and 13B illustrate ROC curves for examinee B. Compared with the case where the temporal correlation width was fixed (as illustrated in FIGS. 12A and 13A), the ROC curves approached to the left uppermost portion when the temporal correlation width of cubic higher-order local autocorrelation (CHLAC) features was varied (as illustrated in FIGS. 12B and 13B). From this, it can be known that the AUC value was higher in FIGS. 12B and 13B than in FIGS. 12A and 13A.

Figure 14A:
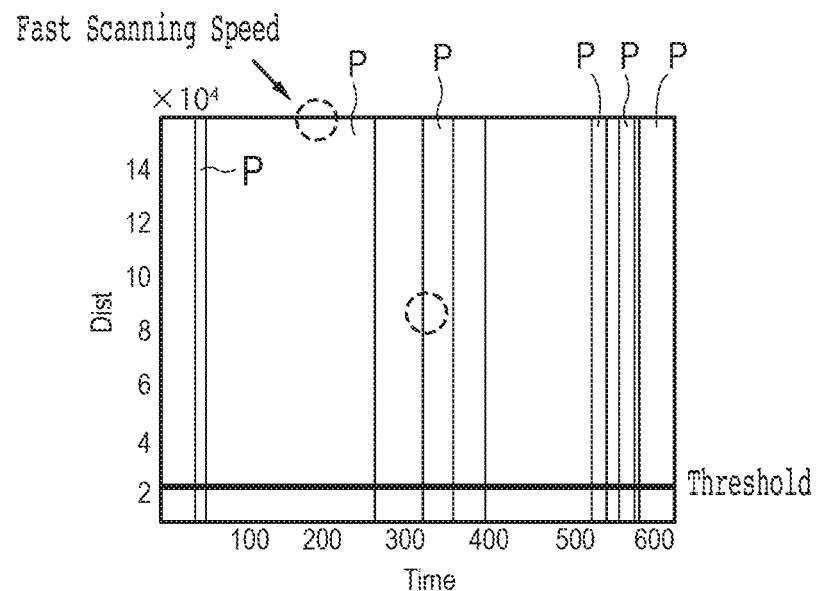
FIGS. 14A and 14B illustrate abnormality detection results for examinees A and B.
Figure 14B:
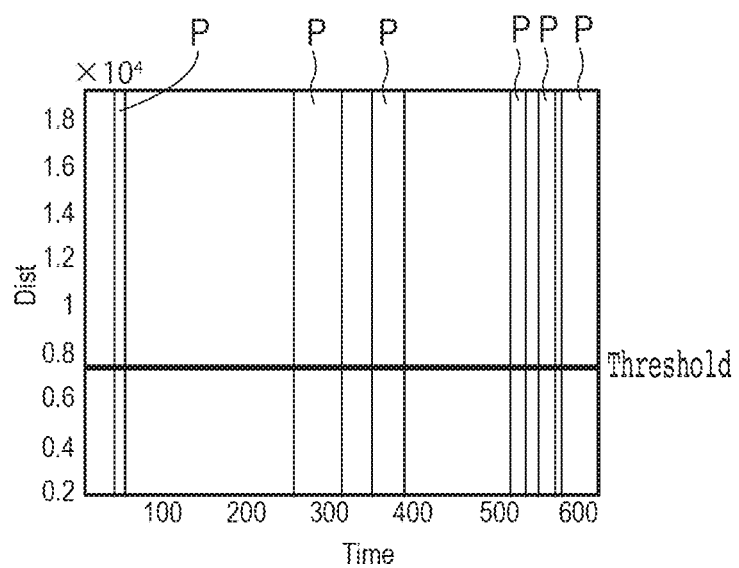
Figure 15A:
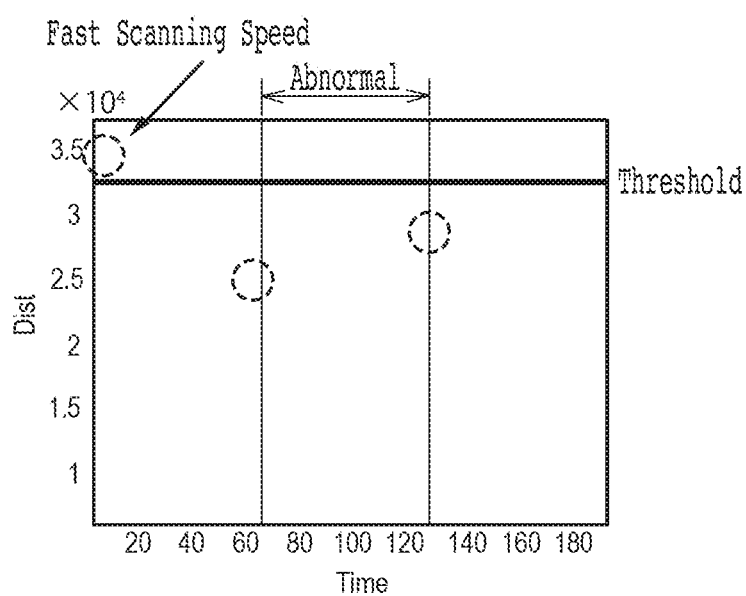
FIGS. 15A and 15B illustrate abnormality detection results for examinees A and B.
Figure 15B:
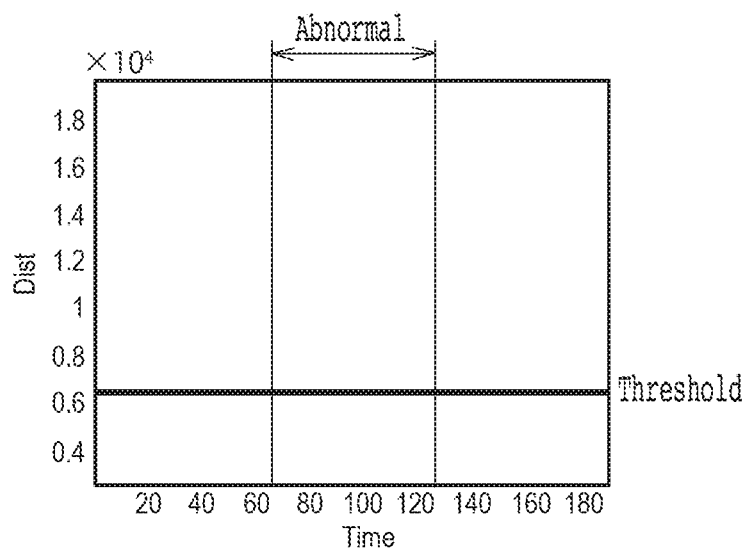

The abnormality detection results from the dynamic images captured from examinees A and B are shown in FIGS. 14 and 15. The black lines in the graph represent the thresholds for determining normality/abnormality. If the distance to the normal subspace was larger than the threshold, that frame was determined as abnormal. In FIGS. 14A and 14B, abnormal frames containing a lesion continuously existed in segments indicated with P. In FIGS. 15A and 15B, abnormal frames containing a lesion continuously existed in segments annotated with "Abnormal". In the abnormality detection results of examinee A, when the temporal correlation width was fixed (refer to FIGS. 14A and 15A), the distance to the normal subspace was large in some cases where the frame was normal, which indicates that many over detections were caused. In contrast therewith, when the temporal correlation width was varied (refer to FIGS. 14B and 15B), the frames containing a lesion tended to show a longer distance to the normal subspace than the normal frames. This indicates that the influence of the scanning speed of the ultrasonic probe could be suppressed by varying the temporal correlation width. For examinee B, although over detections increased, the influence was suppressed in the frames where the scanning speed was fast.

Experiment Method (One-Class SVM as an Analyzing Method)

In the experiment, in order to verify the validity of extraction of cubic higher-order local autocorrelation (CHLAC) features while varying the temporal correlation width according to the scanning speed of the ultrasonic probe, the true positive rates (TP) and false positive rates (FP) in the following two cases were compared: the temporal correlation width of cubic higher-order local autocorrelation (CHLAC) features was fixed; and the temporal correlation width was varied.

The temporal correlation width of cubic higher-order local autocorrelation (CHLAC) features was set to [5, 3, 1] corresponding to the scanning speed [slow, medium, fast]. In the one-class SVM, the Gaussian kernel was used as a kernel function.

Experiment Results (One-Class SVM as an Analyzing Method)

Figures 16A, 16B:
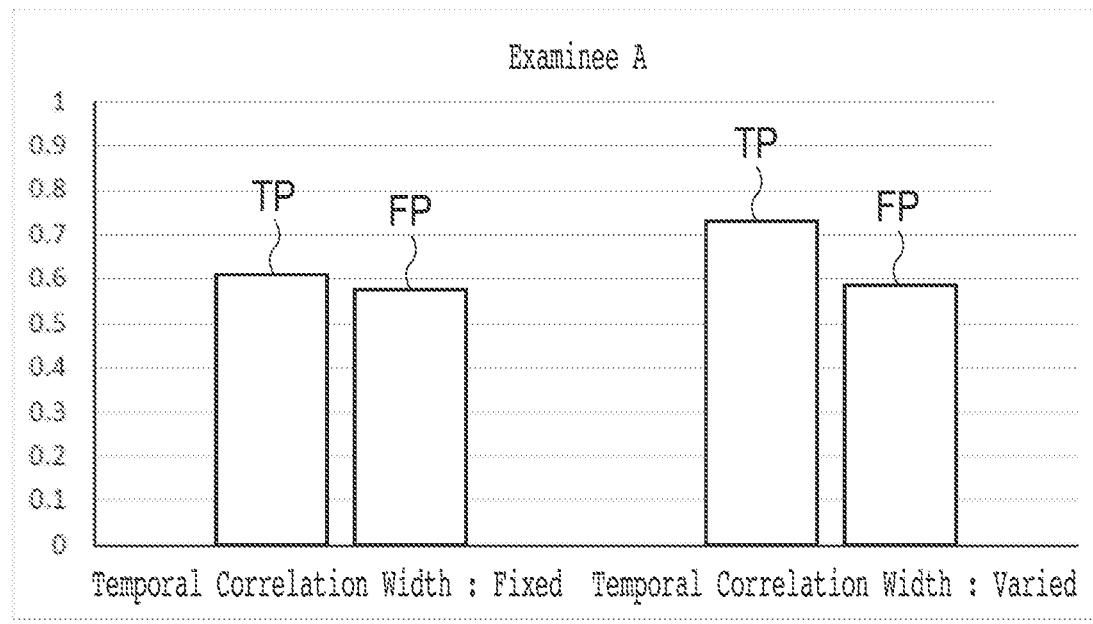
FIGS. 16A and 16B illustrate true and false positive rates for examinee A.
Figures 17A, 17B:
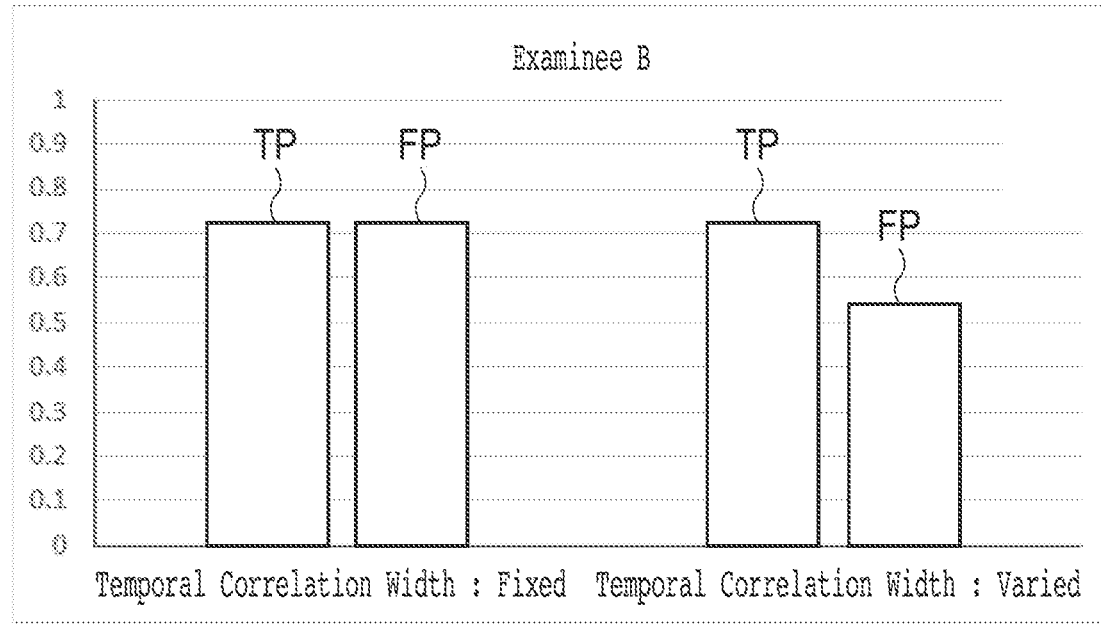
FIGS. 17A and 17B illustrate true and false positive rates for examinee B.

The experiment results of the true positive rate (TP) and the false positive rate (FP) are shown in FIGS. 16 and 17. From FIG. 16, it can be known that the true positive rate was higher when the temporal correlation width of cubic higher-order local autocorrelation (CHLAC) features was varied than when the temporal correlation width was fixed. From FIG. 17, it can be known that there was no difference in true positive rate between the two cases: when the temporal correlation width was fixed and when the temporal correlation width was varied. It can also be known from FIG. 17 that the false positive rate decreased when the temporal correlation width was varied, compared with when the temporal correlation width was fixed. This indicates that over detections could be suppressed when the temporal correlation width was varied. It follows from the foregoing that the influence of the scanning speed of the ultrasonic probe was suppressed by varying the temporal correlation width.

INDUSTRIAL APPLICABILITY

The ultrasound examination system of the present invention is intended to automatically detect a lesion, based on a dynamic image comprised of a plurality of frame arrays that are temporally continuous and are output from the ultrasound examination apparatus with an ultrasonic probe being manipulated. According to the present invention, detection accuracy of the ultrasound examination system can be increased.

DESCRIPTION OF REFERENCE NUMERALS

1 Ultrasonic Probe
3 Ultrasound Examination Apparatus
5 Reference Data Storage
7 Frame Checker
9 Speed Information Acquirer
11 Speed Determinator
71 Feature Extractor
72 State Determinator
73 Distance Calculator
74 Distance Determinator
75 Final Determinator

The invention claimed is:
1. A system for ultrasound examination configured to examine whether or not a lesion exists, based on a dynamic image comprised of a plurality of frames that are temporally continuous and are output from an ultrasound examination apparatus with an ultrasonic probe being manipulated, the system comprising;
 a reference data storage operable to store reference data for determining normality that are obtained by extracting cubic higher-order local autocorrelation features from the plurality of frames that constitute the dynamic image of a human body part where the lesion does not exist as obtained from a reference examinee or an examinee with the ultrasonic probe being manipulated while adjusting, on a basis of ultrasonic probe speed information, a temporal correlation width between the plurality of frames used for extracting the cubic higher-order local autocorrelation features, so as to suppress an influence of changes in speed of the ultrasonic probe to be given to extraction results, and analyzing the extraction results by a predetermined analyzing method;
 a frame checker including:
  a feature extractor operable to extract the cubic higher-order local autocorrelation features from each of the plurality of frames that constitute the dynamic image of the human body part as obtained from the ultrasound examination apparatus while an examiner manipulates the ultrasonic probe on the examinee, and
  a state determinator operable to determine whether a frame in question of said plurality of frames is a normal frame not containing the lesion or an abnormal frame containing the lesion, based on the extraction results of the cubic higher-order local autocorrelation features extracted from each of said plurality of frames and the reference data for determining normality; and
 a speed information acquirer operable to acquire the ultrasonic probe speed information of the ultrasonic probe manipulated by the examiner in respect of each of said plurality of frames,
 wherein:
  the feature extractor has a function of adjusting, on the basis of the ultrasonic probe speed information, the temporal correlation width between the plurality of frames used for extracting the cubic higher-order local autocorrelation features so as to suppress the influence of changes in the speed of the ultrasonic probe to be given to the extraction results;

the state determinator in the frame checker determines, on the basis of the extraction results of the cubic higher-order local autocorrelation features from each of said plurality of frames and the reference data for determining normality, whether the frame in question is the normal frame or the abnormal frame.

2. The system for ultrasound examination according to claim 1, wherein:
the predetermined analyzing method is a subspace method;
the reference data storage stores, as the reference data for determining normality, a normal subspace obtained by performing principal component analysis on the extraction results; and
the state determinator in the frame checker includes:
a distance calculator operable to calculate a distance between the extraction results of cubic higher-order local autocorrelation features from each frame and the normal subspace,
a distance determinator operable to determine whether or not the distance is a normal distance, according to whether or not the distance exceeds a predefined threshold, and
a final determinator operable to determine that the frame in question is the normal frame when the distance determinator determines that the distance is the normal distance and that the frame in question is the abnormal frame when the distance determinator determines that the distance is not the normal distance.

3. The system for ultrasound examination according to claim 2, wherein:
the feature extractor adjusts the temporal correlation width in a weakly monotonically decreasing manner according to a magnitude of the speed of the ultrasonic probe as obtained from the speed information.

4. The system for ultrasound examination according to claim 3, wherein:
the feature extractor is configured to prepare a plurality of speed threshold ranges that stepwisely increase in value and a plurality of temporal correlation widths corresponding to the plurality of speed threshold ranges, to compare the speed of the ultrasonic probe with the plurality of speed threshold ranges, and to select the temporal correlation width corresponding the speed of the ultrasonic probe.

5. The system for ultrasound examination according to claim 2, wherein:
the predefined threshold used in the distance determinator is defined by utilizing ROC analysis.

6. The system for ultrasound examination according to claim 1, wherein:
the predetermined analyzing method used in extracting the reference data for determining normality is a method using a one-class support vector machine, and only normal frames are used to define normal classes of normal frames as the reference data for determining normality; and
the frame checker determines whether or not the frame in question is the normal frame according to whether or not analyzed data for the frame in question belong to the normal classes.

7. The system for ultrasound examination according to claim 1, wherein:
the speed information acquirer calculates the speed information on the speed of the ultrasonic probe from information on a position and a posture of the ultrasonic probe.

8. A method for ultrasound examination that uses a computer to examine whether or not a lesion exists, based on a dynamic image comprised of a plurality of frames that are temporally continuous and are output from an ultrasound examination apparatus with an ultrasonic probe being manipulated, the method using the computer to execute the steps of:
learning to obtain reference data for determining normality by extracting cubic higher-order local autocorrelation features from the plurality of frames that constitute the dynamic image of a human body part where the lesion does not exist as obtained from a reference examinee or an examinee with the ultrasonic probe being manipulated while adjusting, on a basis of ultrasonic probe speed information, a temporal correlation width between the plurality of frames used for extracting the cubic higher-order local autocorrelation features, so as to suppress an influence of changes in speed of the ultrasonic probe to be given to extraction results, and analyzing the extraction results by a predetermined method;
extracting features to extract cubic higher-order local autocorrelation features from each of the plurality of frames that constitute the dynamic image of the human body part as obtained from the ultrasound examination apparatus while an examiner manipulates the ultrasonic probe on the examinee;
checking a frame in question of said plurality of frames to determine whether the frame in question is a normal frame not containing the lesion or an abnormal frame containing the lesion, based on the extraction results of the cubic higher-order local autocorrelation features from each frame of said plurality of frames and the reference data for determining normality; and
acquiring speed information to acquire speed information on the speed of the ultrasonic probe manipulated by the examiner in respect of each of said plurality of frames, wherein:
in the step of checking the frame in question, the temporal correlation width between the plurality of frames used for extracting the cubic higher-order local autocorrelation features is adjusted, on the basis of the ultrasonic probe speed information, so as to suppress the influence of changes in the speed of the ultrasonic probe to be given to the extraction results;
in the step of checking the frame in question, it is determined, on a basis of analyzed data obtained by analyzing the extraction results of cubic the higher-order local autocorrelation features from each of said plurality of frames by the predetermined method, and the reference data for determining normality, whether the frame in question is the normal frame or the abnormal frame.

9. The method for ultrasound examination according to claim 8, wherein:
the predetermined method is a subspace method;
a normal subspace obtained by performing principal component analysis on the extraction results is stored as the reference data for determining normality in the reference data storage; and
the step of checking the frame in question includes the steps of:

calculating a distance between the normal subspace and a subspace obtained by analyzing the extraction results of cubic higher-order local autocorrelation features from each of said plurality of frames, determining a distance to determine whether or not the distance is a normal distance, based on whether or not the distance exceeds a predefined threshold, and determining a state to determine that the frame in question is the normal frame when it is determined in the step of determining a distance that the distance is the normal distance and that the frame in question is the abnormal frame when it is determined in the step of determining a distance that the distance is not the normal distance.

10. The method for ultrasound examination according to claim 8, wherein:

the temporal correlation width is adjusted in a weakly monotonically decreasing manner according to a magnitude of the speed of the ultrasonic probe as obtained from the speed information.

11. The method for ultrasound examination according to claim 10, wherein:

in the step of checking a frame in question, a plurality of speed threshold ranges that stepwisely increase in value and a plurality of temporal correlation widths corresponding to the plurality of speed threshold ranges are prepared; the speed of the ultrasonic probe is compared with the plurality of speed threshold ranges; and the temporal correlation width corresponding the speed of the ultrasonic probe is selected.

12. The method for ultrasound examination according to claim 8, wherein:

the predetermined method used in extracting the reference data for determining normality is a method using a one-class support vector machine, and only normal frames are used to define normal classes of normal frames as the reference data for determining normality; and in the step of checking a frame in question, it is determined whether or not the frame in question is the normal frame according to whether or not analyzed data for the frame in question belong to the normal classes.

* * * * *